(12) United States Patent
Okihara et al.

(10) Patent No.: US 12,343,508 B2
(45) Date of Patent: Jul. 1, 2025

(54) GASKET PRESSING TOOL AND DRUG ADMINISTRATION TOOL USING THE SAME

(71) Applicant: TERUMO KABUSHIKI KAISHA, Tokyo (JP)

(72) Inventors: Hitoshi Okihara, Fujinomiya (JP); Fumiya Matsumoto, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1085 days.

(21) Appl. No.: 17/032,715

(22) Filed: Sep. 25, 2020

(65) Prior Publication Data
US 2021/0008289 A1   Jan. 14, 2021

Related U.S. Application Data

(63) Continuation of application No. PCT/JP2019/012268, filed on Mar. 22, 2019.

(30) Foreign Application Priority Data

Mar. 28, 2018 (JP) .................................. 2018-063372

(51) Int. Cl.
*A61M 5/315*   (2006.01)
(52) U.S. Cl.
CPC .... *A61M 5/31501* (2013.01); *A61M 5/31515* (2013.01)
(58) Field of Classification Search
CPC .......... A61M 5/31501; A61M 5/31515; A61M 5/31505; A61M 5/2033;
(Continued)

(56) References Cited

U.S. PATENT DOCUMENTS 2,221,739 A * 11/1940 Reiter ............... A61M 5/31595
604/135
2004/0122361 A1 * 6/2004 Hart ................ A61M 25/10182
604/97.02
(Continued)

FOREIGN PATENT DOCUMENTS

JP   2017525419 A   9/2017
WO  2015160600 A1   10/2015

OTHER PUBLICATIONS

International Search Report (PCT/ISA/210) mailed on Jun. 25, 2019, by the Japanese Patent Office as the International Searching Authority for International Application No. PCT/JP2019/012268.
(Continued)

*Primary Examiner* — Kevin C Sirmons
*Assistant Examiner* — Leah J Swanson
(74) *Attorney, Agent, or Firm* — BUCHANAN INGERSOLL ROONEY PC

(57) ABSTRACT

A gasket pressing tool includes a syringe attachment member attached to an outer tube, a gasket pressing member that presses a gasket of a syringe, a pressing member biasing body accommodated in the gasket pressing member, a biasing body pressing tubular member that accommodates a rear end portion of the pressing member biasing body and has side portions provided with opening portions, and movement restriction members of the pressing member held by the tubular member and having engagement protrusions that enter through the opening portions of the tubular member. The pressing tool has an engaged state maintaining function for the engagement protrusion of the movement restriction member and the pressing member-side engagement portion of the pressing member, and an operation function for the engagement protrusion for releasing the engagement therebetween.

6 Claims, 29 Drawing Sheets

(58) Field of Classification Search
CPC ........... A61M 2005/31508; A61M 2005/3151; A61M 2005/3139; A61M 5/31526; A61M 5/20; A61M 5/281; A61M 5/3158; A61M 5/31581

See application file for complete search history.

(56) References Cited

U.S. PATENT DOCUMENTS

| | | | |
|---|---|---|---|
| 2005/0101919 A1 | 5/2005 | Brunnberg | |
| 2009/0192460 A1 | 7/2009 | Keller | |
| 2012/0029443 A1 | 2/2012 | Holmqvist | |
| 2013/0338601 A1* | 12/2013 | Cowe | A61M 5/31535 604/189 |
| 2016/0121050 A1* | 5/2016 | Fabien | A61M 5/28 604/228 |

OTHER PUBLICATIONS

Written Opinion (PCT/ISA/237) mailed on Jun. 25, 2019, by the Japanese Patent Office as the International Searching Authority for International Application No. PCT/JP2019/012268.

The extended European Search Report issued Mar. 25, 2021, by the European Patent Office in corresponding European Patent Application No. 19775837.8-1122. (9 pages).

* cited by examiner

GASKET PRESSING TOOL AND DRUG ADMINISTRATION TOOL USING THE SAME

CROSS-REFERENCES TO RELATED APPLICATIONS

This application is a continuation of International Application No. PCT/JP2019/012268 filed on Mar. 22, 2019, which claims priority to Japanese Patent Application No. 2018-063372, filed on Mar. 28, 2018, the entire content of each of which is incorporated herein by reference.

FIELD OF THE INVENTION

The present invention generally relates to a gasket pressing tool that biases a gasket of a syringe in a distal end direction to move the gasket in the distal end direction, and a medicine administration tool using the same.

BACKGROUND DISCUSSION

A conventional prefilled syringe includes an outer tube accommodating liquid medicine, a needle provided at a discharge port of the outer tube, a gasket slidable in the outer tube, and a plunger that presses the gasket in a distal end direction. When such a prefilled syringe accommodates a viscous medicine with high injection resistance, not only self-administration, but also administration operation by a medical worker, can become difficult.

For example, WO 2015/160600 (Patent Literature 1) discloses an injector that assists medication injection by utilizing spring force. This injector includes: a connector having a distal end and a proximal end; a piston rod locked in said connector before medication injection; a spring configured to bias said piston rod distally; a releasable restraining means, where said piston rod moves distally under force of said spring upon release of said releasable restraining means; an activation means configured to release said releasable restraining means upon release of said releasable restraining means; and a mounting means for mounting a syringe at said distal end of said connector.

Patent Literature 1: WO 2015/160600 (US 2017-080159 A1)

SUMMARY

Generally, when the prefilled syringe is used for medicine administration, the entire amount of medicine filled is administered. However, depending on the patient's condition or the like, the medicine administered using the prefilled syringe might need to be interrupted, stopped, or administered in batches.

However, with the injector disclosed in Patent Literature 1, an administration operation that has started continues until the medicine inside is completely discharged. The administration operation cannot be canceled halfway through.

An object of the present disclosure is to provide a gasket pressing tool and a medicine administration tool using the same with which a medicine discharge operation can be performed or assisted, the medicine discharge operation can be easily interrupted, and any desired amount of medicine can be administered.

Disclosed is a gasket pressing tool to move a gasket of a syringe including an outer tube and the gasket in a distal end direction, the outer tube having a rear end portion provided with a flange, the gasket being slidably accommodated in the outer tube, the gasket pressing tool including:

a gasket pressing member capable of pressing the gasket in the distal end direction;

a syringe attachment member attached to the flange of the outer tube;

a pressing member biasing body having a distal end portion accommodated in the gasket pressing member and having a rear end portion protruding from the gasket pressing member;

a biasing body pressing tubular member that accommodates the rear end portion of the pressing member biasing body and has a flange portion that is provided at a distal end portion and is accommodated in the syringe attachment member and an opening portion that is provided at a side portion more on a rear side than the flange portion; and a movement restriction member that is held by the biasing body pressing tubular member and/or the syringe attachment member, includes an engagement protrusion that enters into the biasing body pressing tubular member through the opening portion, and restricts a movement of the gasket pressing member, wherein the gasket pressing member includes a plurality of pressing member-side engagement portions arranged in an axial direction, the pressing member-side engagement portions being capable of engaging with the engagement protrusion of the movement restriction member, and the gasket pressing tool further has an engaged state maintaining function of maintaining a state of engagement between the engagement protrusion of the movement restriction member and the pressing member-side engagement portions of the gasket pressing member, and an engagement protrusion operation function of moving the engagement protrusion to release the engagement between the engagement protrusion and the pressing member-side engagement portion.

Also disclosed is a medicine administration tool including: a syringe that includes an outer tube having a rear end portion provided with a flange and a gasket slidably accommodated in the outer tube; and the gasket pressing tool described above.

DETAILED DESCRIPTION

Figure 1:
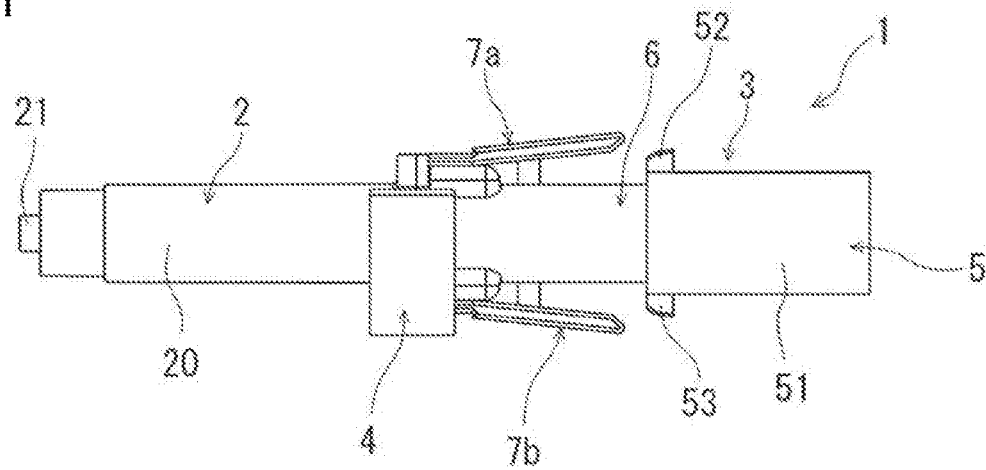
FIG. 1 is a front view of a medicine administration tool including a gasket pressing tool according to an embodiment.
Figure 2:
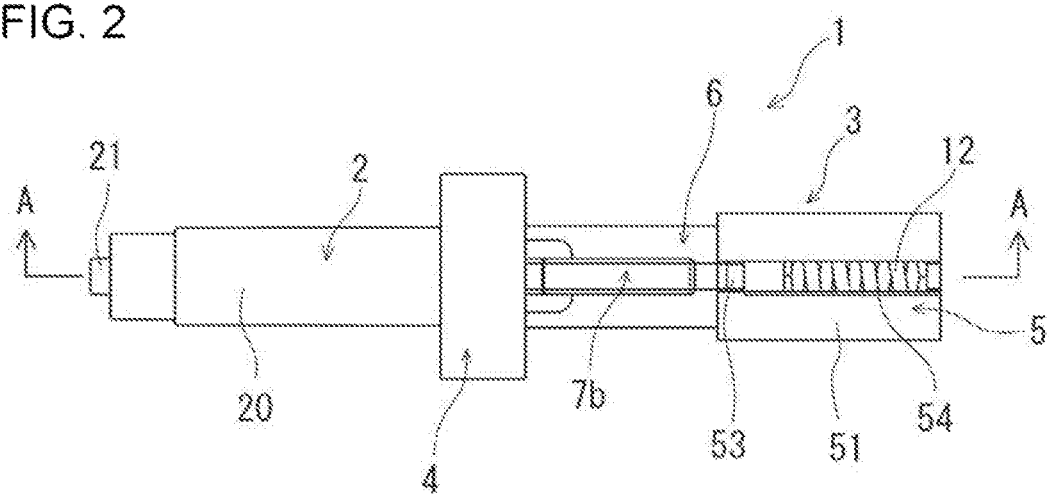
FIG. 2 is a bottom view of the medicine administration tool illustrated in FIG. 1.
Figure 3:
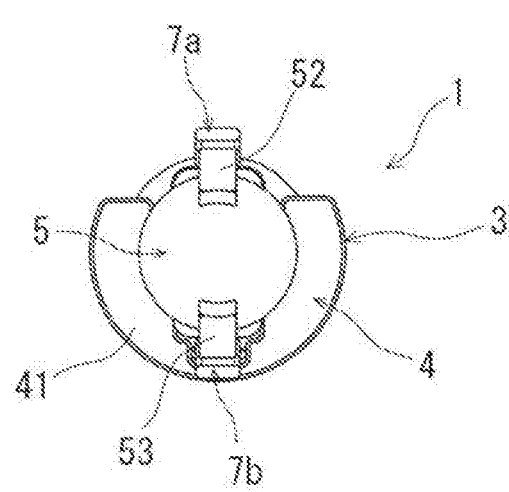
FIG. 3 is a right side view of the medicine administration tool illustrated in FIG. 1.

Set forth below with reference to the accompanying drawings is a detailed description of embodiments of a medicine administration tool and a gasket pressing tool representing examples of the inventive medicine administration tool and gasket pressing tool.

A medicine administration tool 1 includes: a syringe 2 including an outer tube 20 having a rear end portion provided with a flange 23 and a gasket 22 slidably accommodated in the outer tube 20; and a gasket pressing tool 3. As the syringe 2, a prefilled syringe 2a can be used. Furthermore, the medicine administration tool 1 may be in a state where the gasket pressing tool 3 is attached to the prefilled syringe 2a.

Figure 15:
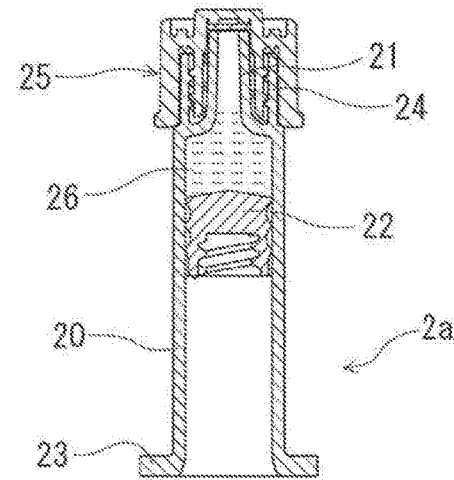
FIG. 15 is a vertical cross-sectional view of an example of a prefilled syringe used for the medicine administration tool.
Figure 16:
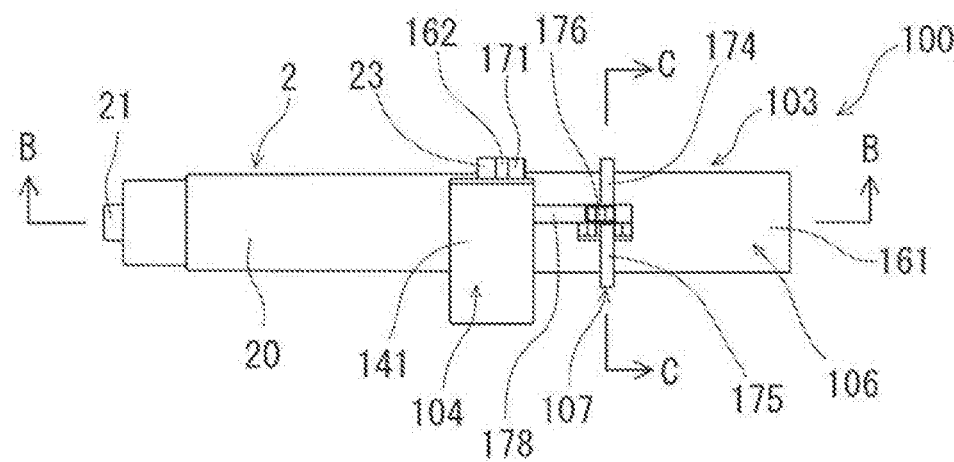
FIG. 16 is a front view of a medicine administration tool including a gasket pressing tool according to another embodiment.
Figure 17:
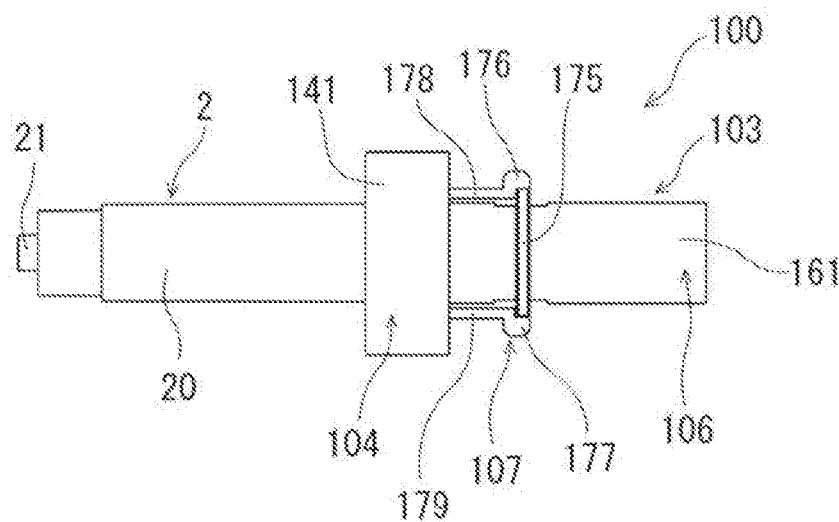
FIG. 17 is a bottom view of the medicine administration tool illustrated in FIG. 16.
Figure 18:
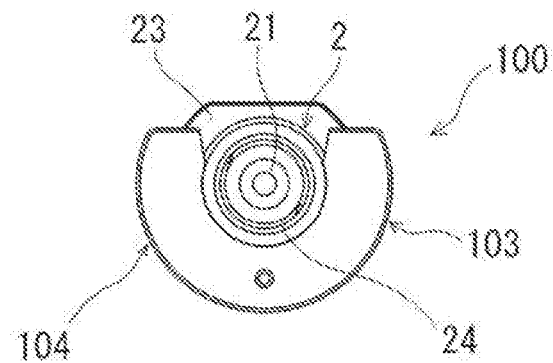
FIG. 18 is a left side view of the medicine administration tool illustrated in FIG. 16.
Figure 19:
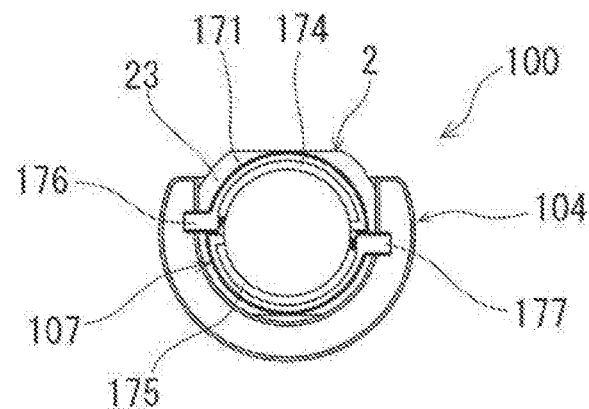
FIG. 19 is a right side view of the medicine administration tool illustrated in FIG. 16.

The prefilled syringe 2a as illustrated in FIG. 15 may be used that includes the outer tube 20 having a tubular portion with a rear end portion provided with the flange 23, the gasket 22 slidably accommodated in the outer tube 20, medicine 26 filling the outer tube 20, and a distal end sealing member 25 of the outer tube 20. The outer tube 20 illustrated includes a nozzle portion 21 and a collar portion 24 that encloses the nozzle portion 21.

The gasket pressing tool 3 biases the gasket 22 of the syringe 2 including the outer tube 20 having the rear end portion provided with the flange 23 and the gasket 22 slidably accommodated in the outer tube 20 in a distal end direction to move the gasket 22 in the distal end direction.

The gasket pressing tool 3 includes: a syringe attachment member 4 that is attached to the flange 23 of the outer tube 20; a gasket pressing member 8 having a tubular shape that can press the gasket 22 in the distal end direction; a pressing member biasing body 11 that has a distal end portion accommodated in the gasket pressing member 8 and has a rear end portion protruding from the gasket pressing member 8; a biasing body pressing tubular member 6 including a flange portion 60 in a distal end portion of the biasing body pressing tubular member 6 that accommodates the rear end portion of the pressing member biasing body 11, and is accommodated in a distal end portion of the syringe attachment member 4, and opening portions 64 and 65 provided at side portions more on the rear side than the flange portion 60 (i.e., proximal to the flange portion 60); and movement restriction members 7a and 7b having a distal end side held by the biasing body pressing tubular member 6 and/or the syringe attachment member 4, having engagement protrusions 72 that enter the inside of the biasing body pressing tubular member 6 through the opening portions 64 and 65, and restricting the movement of the gasket pressing member 8.

The gasket pressing member 8 includes a plurality of pressing member-side engagement portions 83 that are arranged in the axial direction, and can engage with the engagement protrusions 72 of the movement restriction members 7a and 7b. Furthermore, the gasket pressing tool 3 has an engaged state maintaining function of maintaining the state of engagement between the engagement protrusions 72 of the movement restriction members 7a and 7b and the pressing member-side engagement portions 83 of the gasket pressing member 8 and an operation function for the engagement protrusions 72 for moving the engagement protrusions 72 to release the engagement between the engagement protrusions 72 and the pressing member-side engagement portions 83.

First of all, the gasket pressing tool 3 of the embodiment illustrated in FIGS. 1 to 14 will be described.

Figure 4:
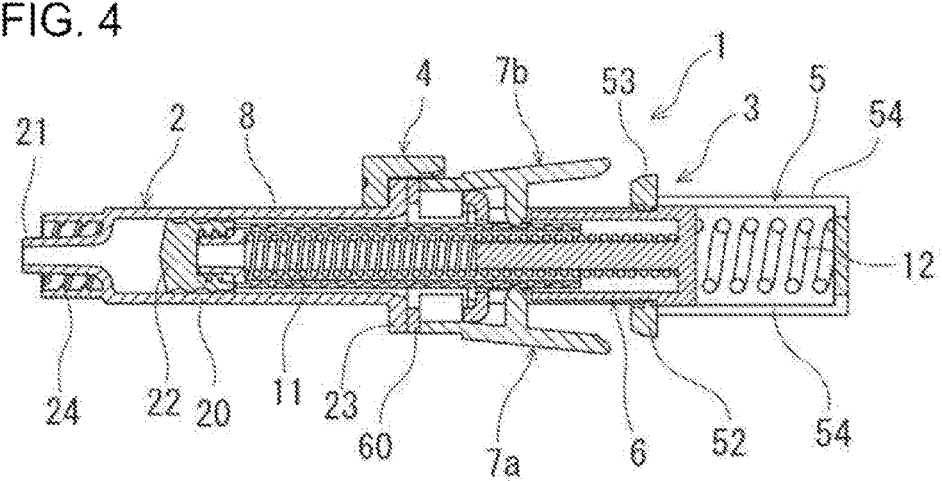
FIG. 4 is a cross-sectional view taken along line A-A illustrated in FIG. 1.
Figure 5:
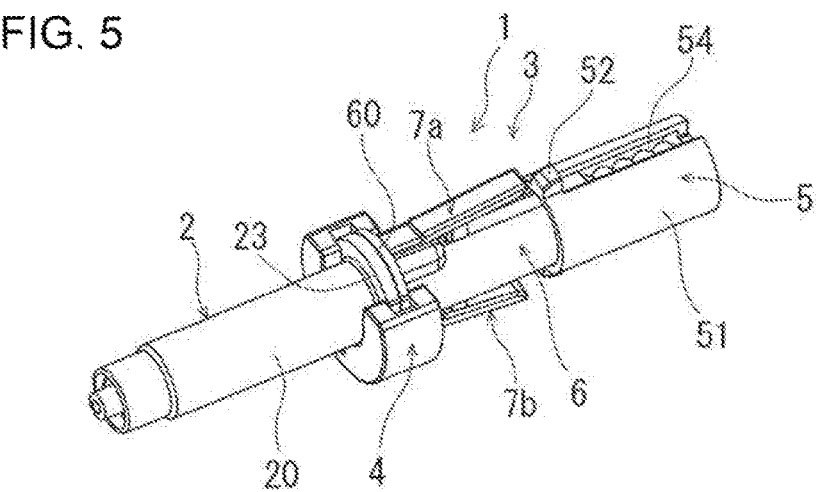
FIG. 5 is a perspective view of the medicine administration tool illustrated in FIG. 1 as seen obliquely from above.
Figure 6:
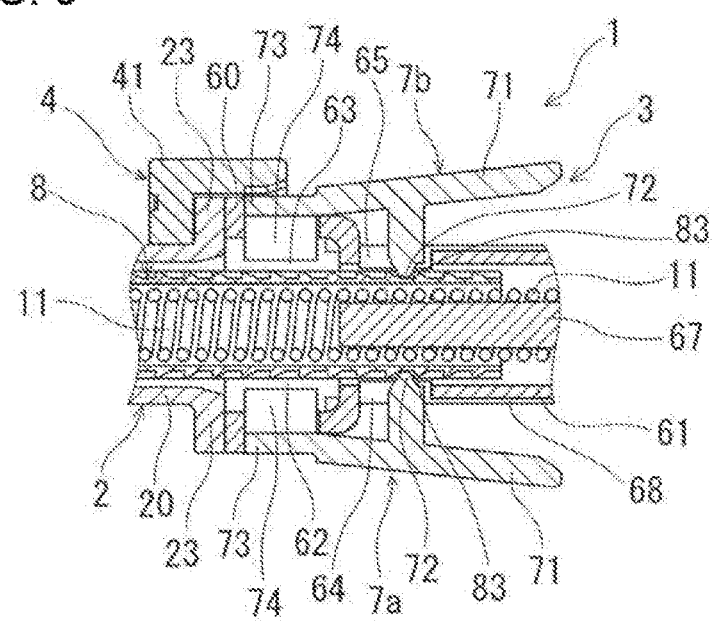
FIG. 6 is an enlarged view of the vicinity of a movement restriction member of the medicine administration tool illustrated in FIG. 4.
Figure 7:
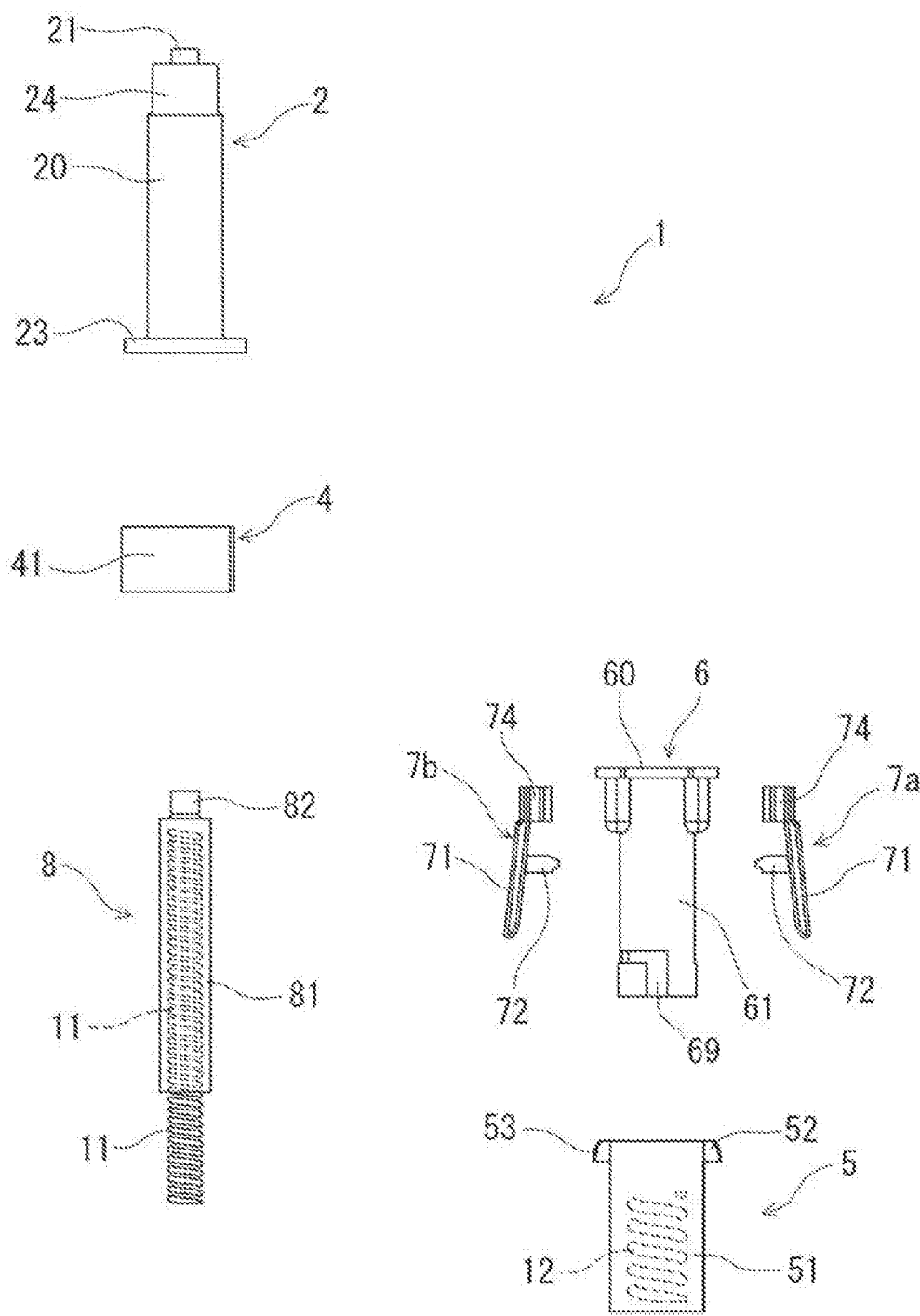
FIG. 7 is an explanatory diagram of components used in the medicine administration tool illustrated in FIG. 1.
Figure 8:
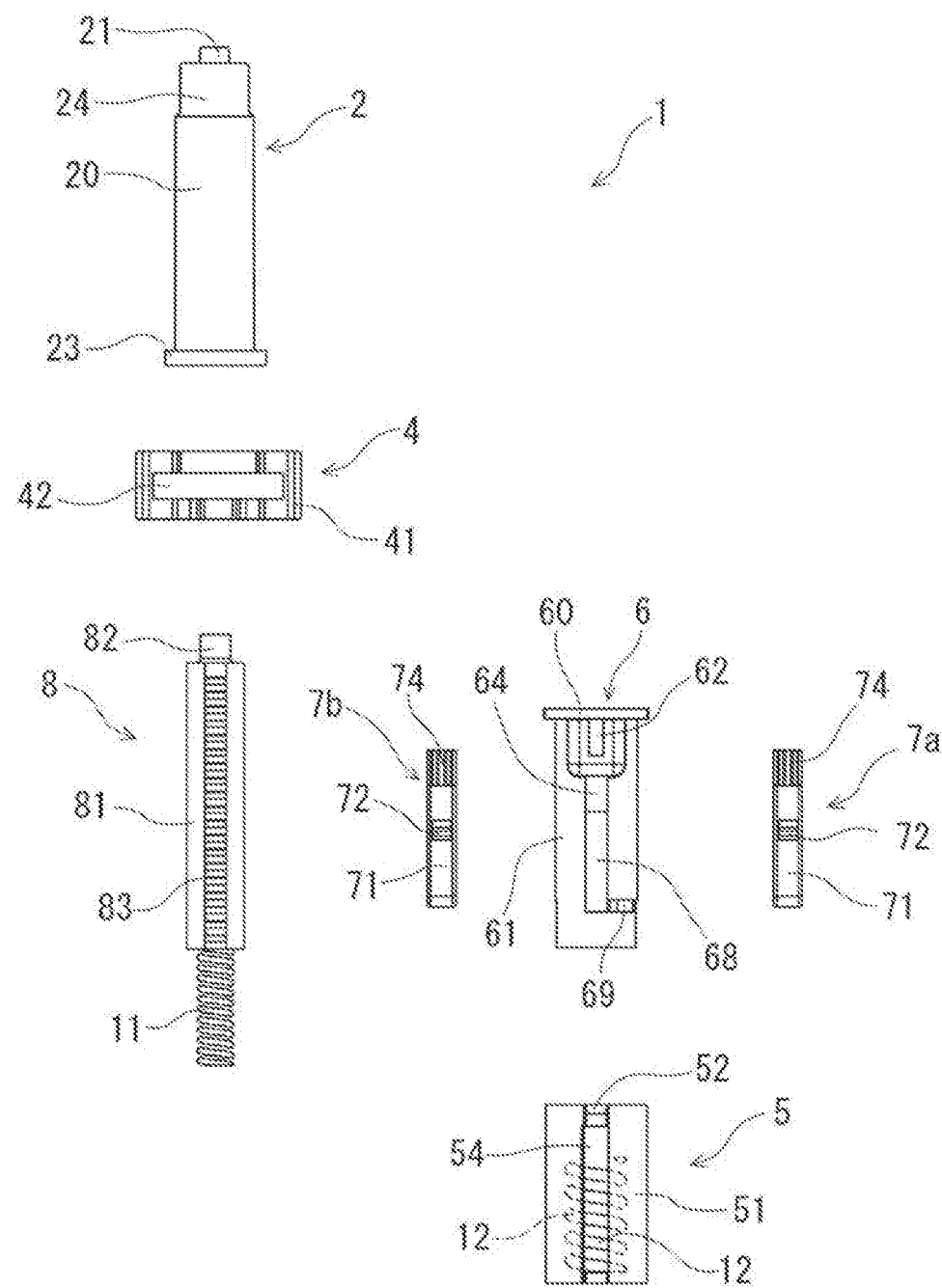
FIG. 8 is an explanatory diagram of components used in the medicine administration tool illustrated in FIG. 1.
Figure 9:
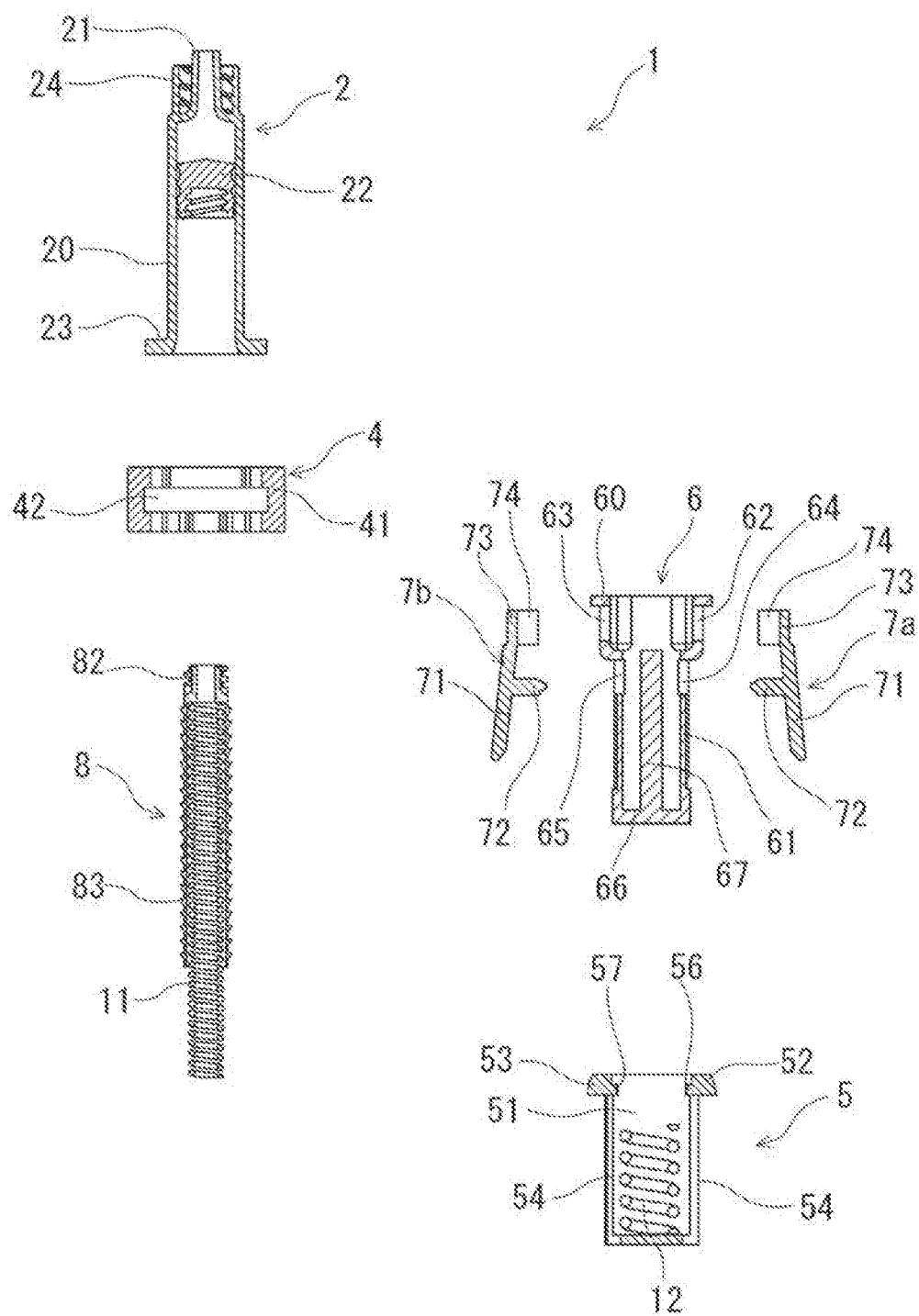
FIG. 9 is an explanatory diagram of components used in the medicine administration tool illustrated in FIG. 1.

As illustrated in FIG. 1 to FIG. 6, the gasket pressing tool 3 of this embodiment has the operation function of releasing the engagement between the engagement protrusion 72 and the pressing member-side engagement portion 83 when an operation member 5 described later is pushed (i.e., longitudinal pushing). To enable this, the movement restriction members 7a and 7b each include: a restriction member main body portion 71 that has a distal end portion held by the biasing body pressing tubular member 6, extends rearward from the distal end portion, and is elastically deformable; and the engagement protrusion 72 that extends in a direction toward the gasket pressing member 8 (that is, a direction from the inner surface toward the center of the gasket pressing tool 3) from the restriction member main body portion 71. As illustrated in FIGS. 4 and 6, the state where the engagement protrusions 72 of the movement restriction members 7a and 7b are engaged with the pressing member-side engagement portions 83 of the gasket pressing member 8 is maintained in a non-operated state, with the restriction member main body portion 71 pressing the engagement protrusion 72 in a direction toward the pressing member-side engagement portion 83 of the gasket pressing member 8. Thus, the engaged state maintaining function is achieved.

Figure 13:
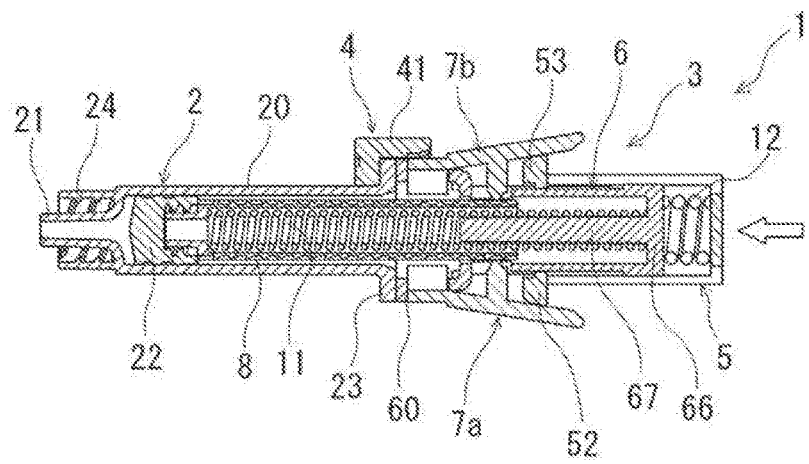
FIG. 13 is an explanatory diagram for explaining an operation of the medicine administration tool illustrated in FIG. 1.
Figure 14:
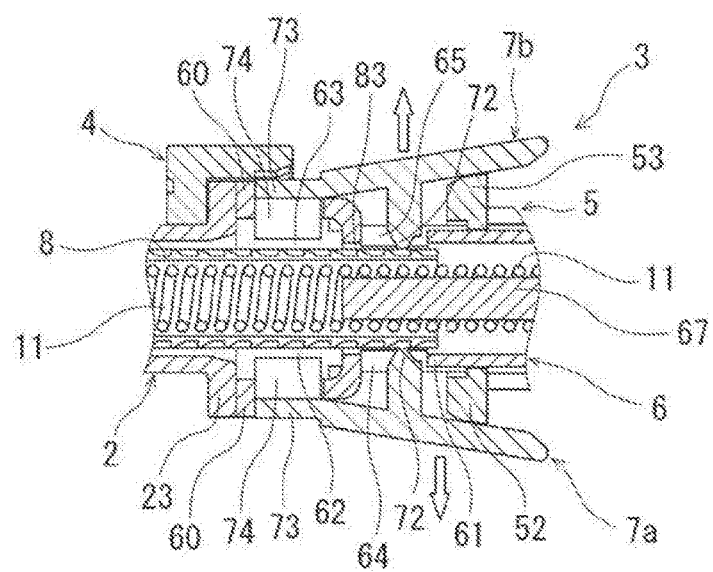
FIG. 14 is an explanatory diagram for explaining an operation of the medicine administration tool illustrated in FIG. 1.

As illustrated in FIGS. 4 and 6 as well as FIGS. 13 and 14, the gasket pressing tool 3 of this embodiment includes the tubular operation member 5 attached to the rear end portion of the biasing body pressing tubular member 6 while being movable in an axial direction, to achieve an engagement protrusion operation function of the gasket pressing tool 3. As illustrated in FIGS. 13 and 14, the operation member 5 includes: engagement releasing protrusion portions 52 and 53 that come into contact with the restriction member main body portions 71 of the movement restriction members 7a and 7b when moving toward the distal end side, to push the restriction member main body portions 71 outward so that the engagement between the engagement protrusions 72 and the pressing member-side engagement portions 83 is released; and an operation member biasing body 12 that is accommodated in the operation member 5, and has a distal end that comes into contact with a rear end surface of the biasing body pressing tubular member 6 to bias the operation member 5 rearward. These components achieve the operation function for the engagement protrusions 72 of moving the engagement protrusions 72 and releasing the engagement between the engagement protrusions 72 and the pressing member-side engagement portions 83.

As illustrated in FIGS. 1 to 14, and in FIGS. 7 to 9, and 12 in particular, the gasket pressing tool 3 of this embodiment includes: the syringe attachment member 4; the tubular gasket pressing member 8; the pressing member biasing body 11 having a distal end side portion accommodated in the gasket pressing member 8; the biasing body pressing tubular member 6 that presses the pressing member biasing body 11 from the rear end side; the two movement restriction members 7a and 7b attached to the biasing body pressing tubular member 6; the operation member 5; and the operation member biasing body 12 that biases the operation member 5 rearward.

As illustrated in FIGS. 1, 4 to 9, and 12, the syringe attachment member 4 includes a main body portion 41 and an accommodation portion 42 formed by an arcuate recess portion extending downward from the upper surface of the main body portion 41. The accommodation portion 42 can accommodate the flange 23 of the outer tube 20 and the flange portion 60 of the biasing body pressing tubular member 6 at the same time. With these components thus accommodated, the gasket pressing tool 3 is attached (coupled) to the syringe 2 (outer tube 20). The syringe attachment member 4 can also be referred to as a syringe coupling member.

The gasket pressing member 8 is a tubular body having a tubular main body portion 81 as illustrated in FIGS. 4, 6 to 9, and 12. The distal end portion is provided with a distal end inner surface portion with which the distal end of the pressing member biasing body 11 accommodated can be in contact (can engage). The outer surface of the distal end portion is provided with an attachment portion 82 for the gasket. Furthermore, the outer surface of the tubular main body portion 81 is provided with the plurality of the pressing member-side engagement portions 83 for engagement that are arranged at an equal interval along the axial direction of the gasket pressing member 8 (tubular main body portion 81).

In this embodiment, the pressing member-side engagement portions 83 are formed by a plurality of ribs formed on the outer surface of the gasket pressing member 8. It should be noted that the pressing member-side engagement portion 83 may have any configuration as long as it includes the front surface that can come into contact with (engage with) the rear surface of the engagement protrusion 72. For example, the outer surface of the gasket pressing member 8 (tubular main body portion 81) may be provided with a plurality of groove portions having front surfaces that can come into contact with (engage with) the rear surfaces of the engagement protrusions 72.

In this embodiment, the gasket pressing member 8 includes a protrusion provided longitudinal side including the plurality of pressing member-side engagement portions 83. Further, in this embodiment, two protrusion provided longitudinal sides, including the plurality of pressing member-side engagement portions 83, are formed opposite to each other on the gasket pressing member 8. The gasket pressing member 8 has a distal end portion (specifically, the distal end surface of the tubular main body portion 81 or the gasket attachment portion 82) that can come into contact with the rear end portion of the gasket 22, and can press the gasket 22.

Furthermore, the gasket pressing member 8 includes the plurality of pressing member-side engagement portions 83 adjacently arranged, as well as gaps into which the engagement protrusions 72 can enter from the outer surface side, the gaps each formed between the pressing member-side engagement portions 83 adjacent to each other in the axial direction.

Preferably, a compressible coil spring is used as the pressing member biasing body 11, as illustrated in FIGS. 4 and 7 to 9. The pressing member biasing body 11 may be a compressible tube-shaped elastic body. The pressing member biasing body 11 is longer in length than the inner cavity of the tubular main body portion 81 of the gasket pressing member 8, has the distal end side accommodated in the gasket pressing member 8, and has a rear end portion that protrudes from the rear end of the gasket pressing member 8 in a state illustrated in FIGS. 4 and 7 to 9, where the distal end surface is in contact with the distal end inner surface portion of the tubular main body portion 81.

As illustrated in FIG. 4, the biasing body pressing tubular member 6 is a member for pressing the pressing member biasing body 11 from the rear end side. As illustrated in FIGS. 4, 7 to 9, and 12, the biasing body pressing tubular member 6 includes: a tubular main body portion 61; the flange portion 60 provided at the distal end portion of the main body portion 61; the opening portions 64 and 65 through which the engagement protrusions 72 of the movement restriction members 7a and 7b enter as described later, the opening portions 64 and 65 being provided at the side portions that are more on the rear side than the flange portion 60; attachment portions 62 and 63 for the movement restriction members 7a and 7b provided between the opening portions 64 and 65 and the flange portion 60; a bar shaped portion 67 that protrudes in the distal end direction from the rear end inner surface (bottom surface portion 66) and can enter the inside of the pressing member biasing body 11; and two axial direction recess portions 68 that are positioned more on the rear side than the opening portions 64 and 65 and extend rearward in the axial direction.

Figure 12:
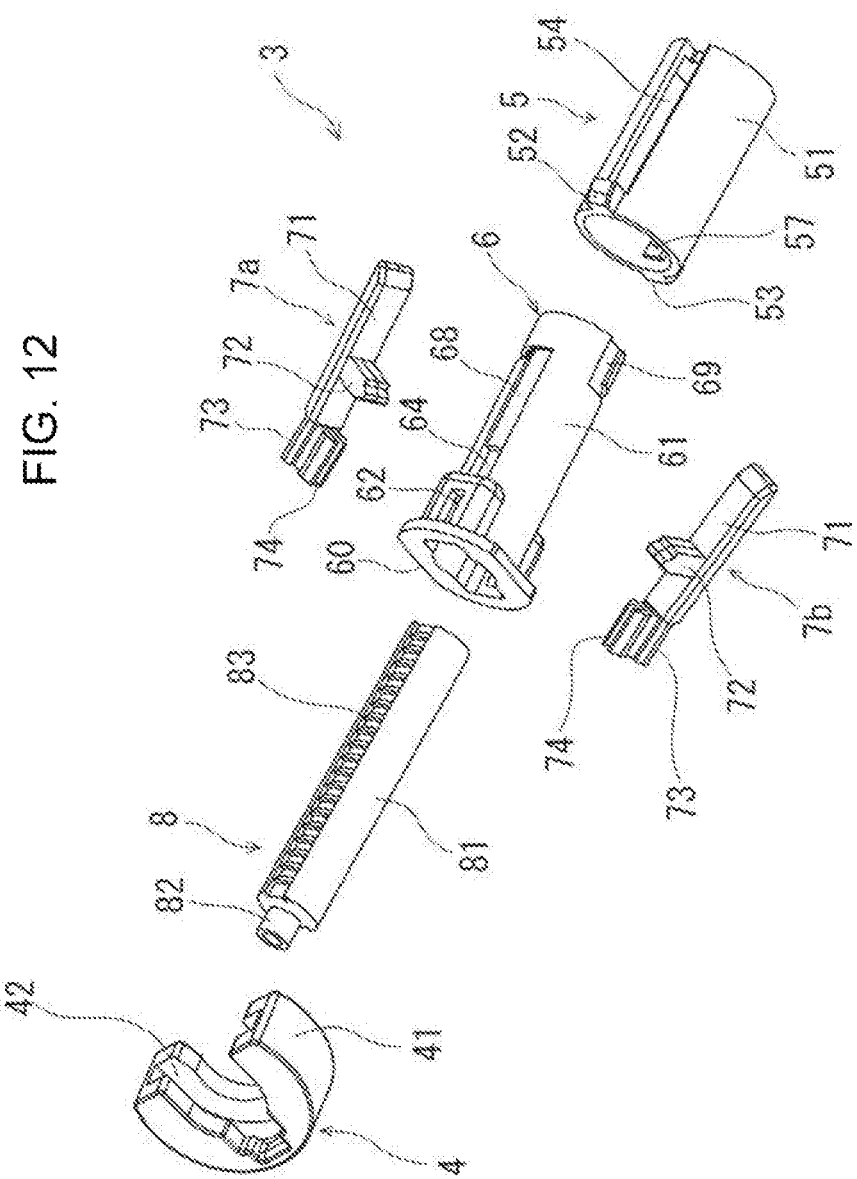
FIG. 12 is an explanatory view of components of the gasket pressing tool used in the medicine administration tool illustrated in FIG. 1.

Furthermore, the biasing body pressing tubular member 6 includes a guiding groove portion 69 including a circumferential groove portion extending in a circumferential direction from the rear end of each axial direction recess portion 68, and an axial direction groove portion extending in the axial direction from an end of the circumferential groove portion. Portions of the biasing body pressing tubular member 6 where the attachment portions 62 and 63 for the movement restriction members 7a and 7b are formed are bulging portions as illustrated in FIG. 12. The tubular main body portion 61 can accommodate the rear end portion of the pressing member biasing body 11. The bar shaped portion 67 enters into the pressing member biasing body 11, to restrict curving deformation of the pressing member biasing body 11 when the compressing (pressing) occurs in the pressing member biasing body 11.

As illustrated in FIGS. 4 to 14, the movement restriction members 7a and 7b each include: the restriction member main body portion 71 that is elastically deformable; the engagement protrusion 72 that extends in the direction toward the gasket pressing member 8 from the main body portion 71 (that is, the direction from the inner surface toward the center of the gasket pressing tool 3); and the attachment portion 74 for the biasing body pressing tubular member 6 provided at the distal end portion 73. The movement restriction members 7a and 7b of this embodiment each have the restriction member main body portion 71 including a highly elastically deformable portion at a rear end portion of the distal end portion 73. Thus, the movement restriction members 7a and 7b can move up and down with the rear end of the distal end portions 73 of the restriction member main body portions 71 as the fulcrum.

Figure 10:
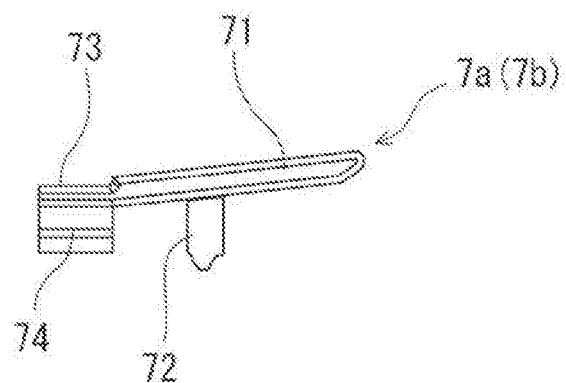
FIG. 10 is a front view of the movement restriction member used in the medicine administration tool illustrated in FIG. 1.
Figure 11:
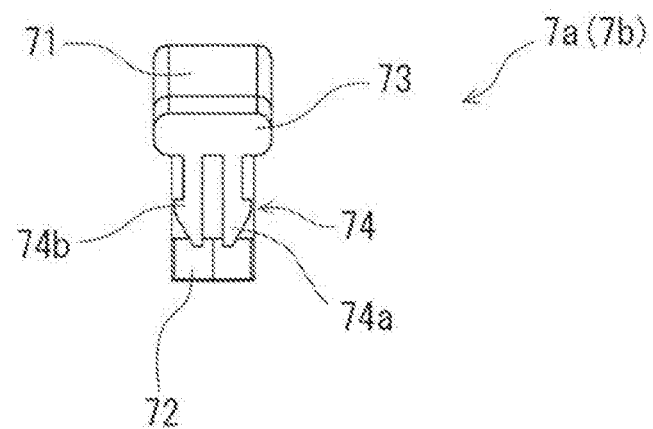
FIG. 11 is a left side view of the movement restriction member illustrated in FIG. 10.

In this embodiment, the two movement restriction members 7a and 7b are provided to face each other. Further, as illustrated in FIGS. 10 and 11, the attachment portion 74 is formed by two leg portions 74a and 74b protruding from the lower surface of the distal end portion 73. The leg portions 74a and 74b each include: a distal end inclined surface; and a retaining portion formed at a rear end portion of the distal end inclined surface.

The movement restriction members 7a and 7b are attached with the attachment portions 74 inserted in the attachment opening portions 64 and 65 of the biasing body pressing tubular member 6, specifically, with the two leg portions 74a and 74b inserted from the distal end inclined surface side and with the retaining portions provided through the attachment opening portions 64 and 65. The retaining portions of the attachment portions 74 engage with the inner surface of the biasing body pressing tubular member 6 near the attachment opening portions 64 and 65, whereby the movement restriction members 7a and 7b are less likely to be detached from the biasing body pressing tubular member 6, even when the restriction member main body portions 71 are pushed upward.

As illustrated in FIGS. 4, 5, and 7 to 13, the operation member 5 includes: the tubular main body portion 51; the engagement releasing protrusion portions 52 and 53 provided on the outer surface of the distal end portion of the main body portion 51; a window portion 54 extending in the axial direction; and sliding protrusions 56 and 57 provided on the inner surface of the distal end portion of the tubular main body portion 51 that is the inner side of the engagement releasing protrusion portions 52 and 53. The engagement releasing protrusion portions 52 and 53 of the operation member 5 include inclined surfaces inclined in the center axis direction and the distal end direction to be in contact with the lower surface of the restriction member main body portion 71.

The sliding protrusions 56 and 57 enter the inside of the axial direction recess portion 68 of the biasing body pressing tubular member 6 to enable the operation member 5 slide in the axial direction of the biasing body pressing tubular member 6, and guides the engagement releasing protrusion portions 52 and 53 of the operation member 5 to the lower surfaces (inner surfaces) of the restriction member main body portions 71. The sliding protrusions 56 and 57 are inserted from the rear end of the axial direction groove portions of the guiding groove portions 69 of the biasing body pressing tubular member 6. When the operation member 5 is rotated after the sliding protrusions 56 and 57 reach the circumferential groove portions, the sliding protrusions 56 and 57 can enter the axial direction recess portions 68. Furthermore, the circumferential groove portion of the guiding groove portion 69 is provided with a retaining rib.

As illustrated in FIGS. 4, 5, and 7 to 13, the operation member biasing body 12 is accommodated in the operation member 5 (in the tubular main body portion 51). A compressible coil spring is preferably used as the operation member biasing body 12. The operation member biasing body 12 may be a compressible tubular elastic body. As illustrated in FIGS. 4 and 13, the operation member biasing body 12 has a distal end that comes into contact with the rear end outer surface of the biasing body pressing tubular member 6, has a rear end that comes into contact with the rear end inner surface of the operation member 5, and can be pressed (compressed) by these surfaces. The compressed operation member biasing body 12 presses (biases) the operation member 5 rearward.

In the gasket pressing tool 3 of this embodiment, the two opening portions 64 and 65 of the biasing body pressing tubular member 6 are provided to face each other, the two engagement protrusions 72 of the movement restriction members 7a and 7b are provided to face each other, and the two engagement releasing protrusion portions 52 and 53 of the operation member 5 are provided to face each other, respectively.

When the gasket pressing tool 3 of this embodiment is in a state illustrated in FIGS. 4 and 6, the pressing member biasing body 11 is compressed between the distal end inner surface of the gasket pressing member 8 and the rear end inner surface of the biasing body pressing tubular member 6, and thus is biasing the gasket pressing member 8 in the distal end direction.

In the gasket pressing tool 3 of this embodiment, as illustrated in FIGS. 4 and 6, the movement restriction members 7a and 7b are attached to the biasing body pressing tubular member 6 so as to be pushed up outward. The engagement protrusions 72 that have been inserted through the opening portions 64 and 65 of the biasing body pressing tubular member 6 are pressed against the outer surface of the gasket pressing member 8, that is, in a state of pressing the outer surface of the gasket pressing member 8.

Thus, in the gasket pressing tool 3 of this embodiment, the engagement protrusions 72 of the movement restriction members 7a and 7b are maintained in the state of being engaged with the pressing member-side engagement portions 83 of the gasket pressing member 8. In the state illustrated in FIGS. 4 to 6 (normal state, the state illustrated in FIGS. 1 and 2), the engagement protrusion 72 enters a gap between the two pressing member-side engagement portions 83, with the rear surface of the distal end portion of the engagement protrusion 72 being in contact with the front surface of any of the pressing member-side engagement portion 83. Thus, the engaged state is achieved. With the engagement protrusion 72 and the pressing member-side engagement portion 83 thus engaged with each other, the movement of the gasket pressing member 8 biased by the pressing member biasing body 11 in the distal end direction is restricted.

In the gasket pressing tool 3 of this embodiment, as illustrated in FIG. 4, the operation member 5 is biased rearward by the biasing member 12 relative to the biasing body pressing tubular member 6. Thus, the operation member 5 is moved furthest toward the rear side. Specifically, as illustrated in FIG. 4, the sliding protrusions 56 and 57 of the operation member 5 are in contact with the rear ends of the axial direction recess portions 68 of the biasing body pressing tubular member 6.

As illustrated in FIG. 13, when the operation member 5 is pushed in a direction indicated by the arrow, the operation member 5 moves in the distal end direction. Then, as illustrated in FIG. 14, the engagement releasing protrusion portions 52 and 53 of the operation member 5 come into contact with the inner surfaces (lower surfaces) of the restriction member main body portions 71 of the movement restriction member 7, to push up the restriction member main body portions 71 in the direction indicated by an arrow (outward). The outward movement of the restriction member main body portion 71 causes the outward movement of the engagement protrusion 72. As a result, the engagement protrusion 72 is no longer engaged with the pressing member-side engagement portion 83, and the engagement between these members is thus released. Thus, with the biasing body 12, the gasket pressing member 8 presses the gasket 22 to move the gasket 22 in the distal end direction.

When the pressing of the operation member 5 stops, in the gasket pressing tool 3 of this embodiment, the operation member 5 is immediately pushed back toward the rear side by the biasing body 12, and thus retracts to the position illustrated in FIG. 4. When the operation member 5 is retracted, the engagement releasing protrusion portions 52 and 53 are also retracted, and thus the restriction member main body portion 71 is no longer pushed up outward. The engagement protrusion 72 is pushed down by the elastic deformation force to return to the original form, and thus is engaged again with the pressing member-side engagement portion 83. Thus, the gasket pressing member 8 and the gasket 22 also stop moving.

Thus, with the gasket pressing tool 3 of this embodiment, the medicine can be administered only when the operation member 5 is pressed in the direction indicated by the arrow. Furthermore, the pressing member biasing body 11 assists the medicine administration.

Next, a medicine administration tool 100 and a gasket pressing tool 103 of an embodiment illustrated in FIGS. 16 to 30 will be described.

The medicine administration tool 100 of this embodiment includes: a syringe 2 including an outer tube 20 having a rear end portion provided with a flange 23 and a gasket 22 slidably accommodated in the outer tube 20; and the gasket pressing tool 103. As the syringe 2, a prefilled syringe 2a can be used. Furthermore, the medicine administration tool 100 may be in a state where the gasket pressing tool 103 is attached to the prefilled syringe 2a.

As illustrated in FIG. 16 to FIG. 30, the gasket pressing tool 103 of this embodiment has an operation function of releasing the engagement between engagement protrusions 172 and 173 and pressing member-side engagement portions 183, with operation pressing portions 176 and 177 of a movement restriction member 107 pushed toward the center side (i.e., lateral pressing), as described later.

As illustrated in FIGS. 20 to 23, the movement restriction member 107 of the gasket pressing tool 103 of this embodiment includes an operation unit including: a ring-shaped distal end portion 171 held by a biasing body pressing tubular member 106 and/or a syringe attachment member 104; the engagement protrusions 172 and 173 that are positioned more on the rear side than the distal end portion 171 and provided in one end portion; the operation pressing portions 176 and 177; frames 174 and 175 that couple the engagement protrusions 172 and 173 and the operation pressing portions 176 and 177 to each other. The gasket pressing tool 103 includes pressing portion biasing bodies 115 and 116 that are disposed between each of the operation pressing portions 176 and 177 of the movement restriction member 107 and the biasing body pressing tubular member 106 and bias the operation pressing portions 176 and 177 outward. These components achieve the engaged state maintaining function.

As illustrated in FIGS. 20 to 23, in the gasket pressing tool 103 of this embodiment, the engagement between the engagement protrusions 172 and 173 of the movement restriction member 107 and the pressing member-side engagement portions 183 of the gasket pressing member 108 is released, with the engagement protrusions 172 and 173 moved in the outward direction together with the frames 174 and 175 in response to the pressing of the operation pressing portions 176 and 177.

When the pressing of the operation pressing portions 176 and 177 is released, the pressing portion biasing bodies 115 and 116 push back the operation pressing portions 176 and 177. As a result, the engagement protrusions 172 and 173 move in the inward direction together with the frames 174 and 175, whereby the engagement protrusions 172 and 173 of the movement restriction member 107 again engage with the pressing member-side engagement portions 183 of the gasket pressing member 108.

Figure 20:
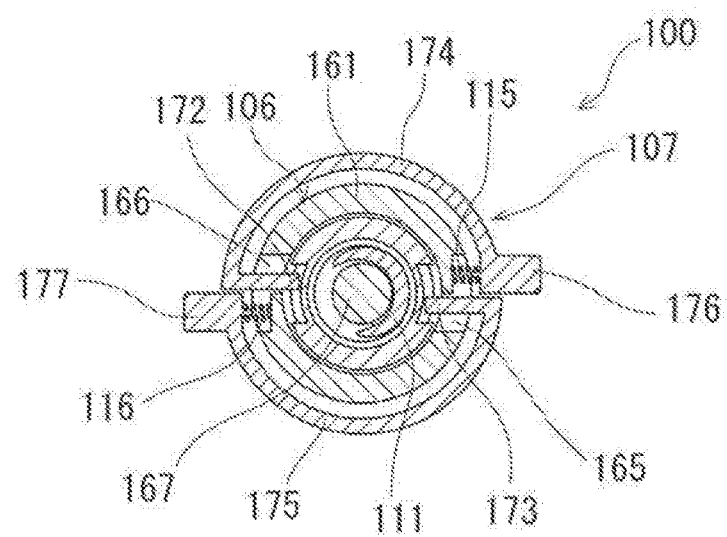
FIG. 20 is a cross-sectional view taken along line C-C of FIG. 16.

In the gasket pressing tool 103 of this embodiment, as illustrated in FIG. 20, the syringe attachment member 104 has two opening portions 165 and 166 of the biasing body pressing tubular member 106 facing each other, two operation units including the engagement protrusions, the operation pressing portion, and the frames facing each other, and two pressing portion biasing bodies 115 and 116 facing each other, respectively.

Figure 23:
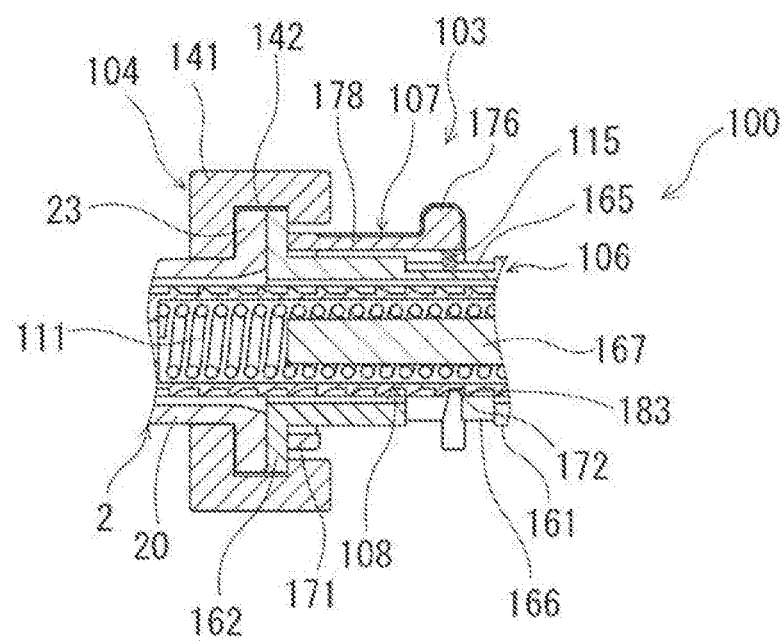
FIG. 23 is an enlarged view of the vicinity of a movement restriction member of the medicine administration tool illustrated in FIG. 21.
Figure 24:
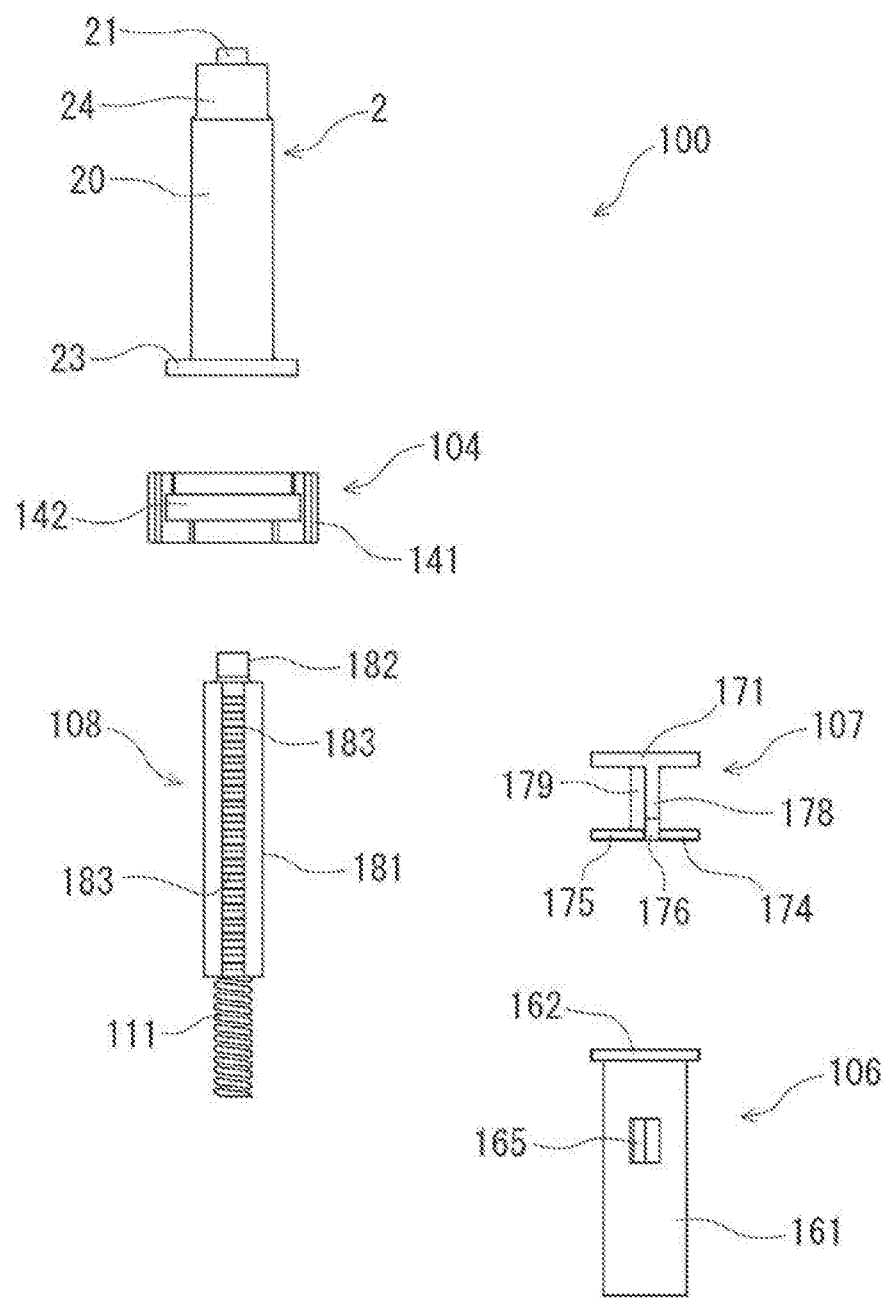
FIG. 24 is an explanatory diagram of components used in the medicine administration tool illustrated in FIG. 16.
Figure 25:
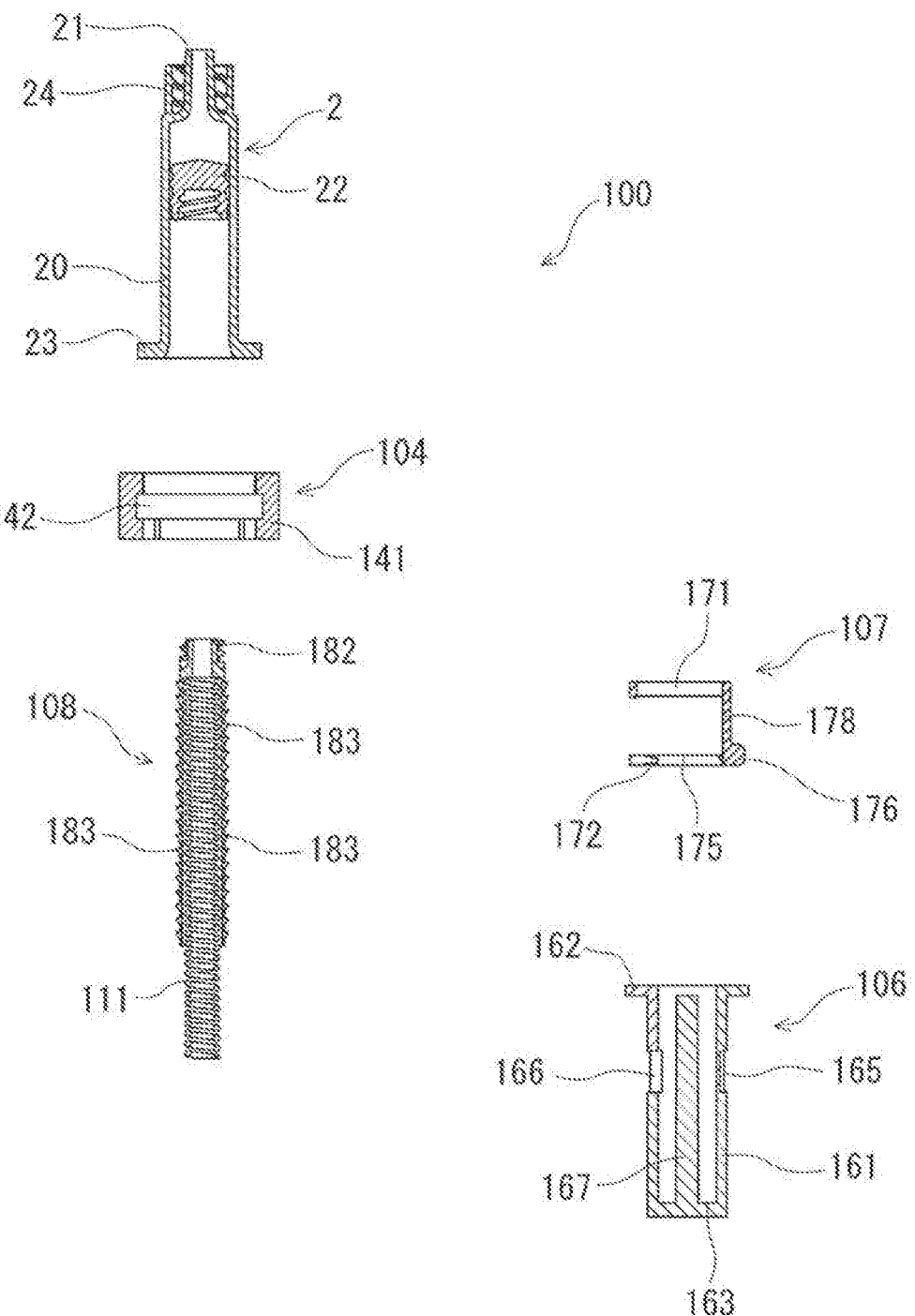
FIG. 25 is an explanatory diagram of components used in the medicine administration tool illustrated in FIG. 16.
Figure 26:
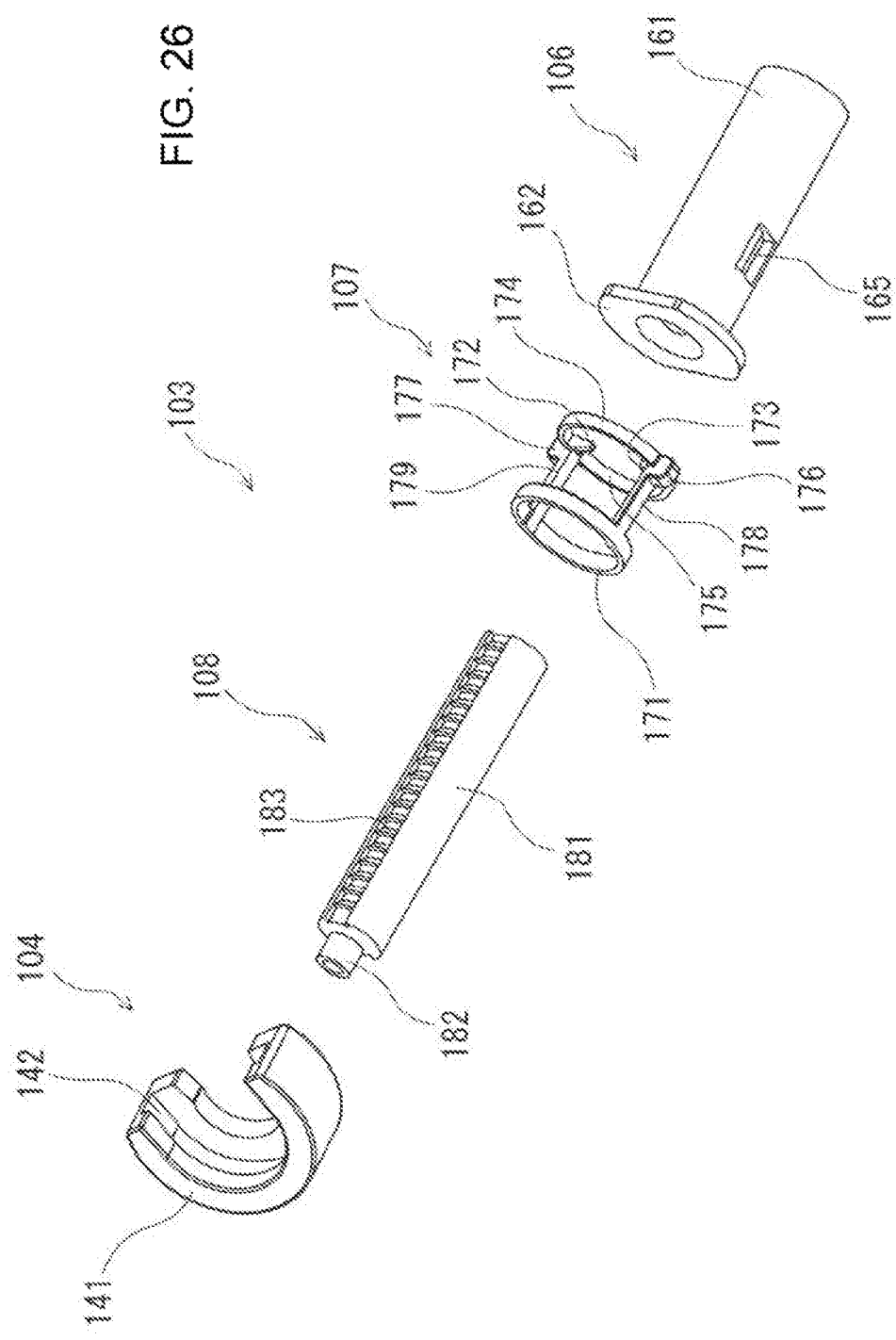
FIG. 26 is an explanatory view of components of the gasket pressing tool used in the medicine administration tool illustrated in FIG. 16.
Figure 27:
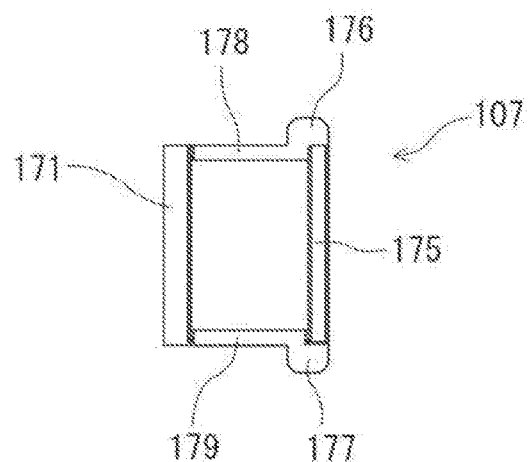
FIG. 27 is a bottom view of the movement restriction member used in the medicine administration tool illustrated in FIG. 16.

As illustrated in FIGS. 16 to 26, and in FIGS. 24 to 26 in particular, the gasket pressing tool 103 of this embodiment includes: the syringe attachment member 104; the tubular gasket pressing member 108; a pressing member biasing body 111 having a distal end side portion accommodated in the gasket pressing member 108; the biasing body pressing tubular member 106 that presses the pressing member biasing body 111 from the rear end side; and the movement restriction member 107.

As illustrated in FIGS. 16 to 26, the syringe attachment member 104 includes a main body portion 141 and an accommodation portion 142 formed by an arcuate recess portion extending downward from the upper surface of the main body portion 141. The accommodation portion 142 can accommodate the flange 23 of the outer tube 20 and a flange portion 162 of the biasing body pressing tubular member 106 at the same time. With these components thus accommodated, the gasket pressing tool 103 is attached (coupled) to the syringe 2 (outer tube 20). The syringe attachment member 104 can also be referred to as a syringe coupling member.

The gasket pressing member 108 is a tubular body having a tubular main body portion 181 as illustrated in FIGS. 21 and 24 to 26. The distal end portion is provided with a distal end inner surface portion with which the distal end of the pressing member biasing body 111 accommodated can be in contact. The outer surface of the distal end portion is provided with an attachment portion 182 for the gasket. The outer surface of the tubular main body portion 181 is provided with the plurality of pressing member-side engagement portions 183 for engagement that are arranged at an equal interval along the axial direction of the gasket pressing member 108 (tubular main body portion 181).

In other words, the gasket pressing member 108 includes a protrusion provided longitudinal side including the plurality of pressing member-side engagement portions 183. Furthermore, in this embodiment, two protrusion provided longitudinal sides, including the plurality of pressing member-side engagement portions 183, are formed opposite to each other. The gasket pressing member 108 has a distal end portion (specifically, the distal end surface of the tubular main body portion 181 or the gasket attachment portion 182) that can come into contact with the rear end portion of the gasket 22, and thus can press the gasket 22.

Furthermore, the gasket pressing member 108 includes the plurality of pressing member-side engagement portions 183 adjacently arranged, as well as gaps into which the engagement protrusions 172 and 173 can enter from the outer surface side, the gaps each formed between the pressing member-side engagement portions 183 adjacent to each other in the axial direction.

In this embodiment, the pressing member-side engagement portions 183 are formed by a plurality of ribs formed on the outer surface of the gasket pressing member 108. It should be noted that the pressing member-side engagement portion 183 may have any configuration as long as it has the front surface that can come into contact with (engage with) the rear surface of the engagement protrusion 172. For example, the outer surface of the gasket pressing member 108 (tubular main body portion 181) may be provided with a plurality of groove portions having front surfaces that can come in contact with (engage with) the rear surfaces of the engagement protrusions 172.

Preferably, a compressible coil spring is used as the pressing member biasing body 111, as illustrated in FIGS. 21 and 24 to 26. The pressing member biasing body 111 may be a compressible tube-shaped elastic body. The pressing member biasing body 111 is longer in length than the inner cavity of the tubular main body portion 181 of the gasket pressing member 108, has the distal end side accommodated in the gasket pressing member 108, and has a rear end portion that protrudes from the rear end of the gasket pressing member 108 in a state illustrated in FIGS. 21 and 24 to 26, where the distal end surface is in contact with the distal end inner surface portion of the tubular main body portion 181.

Figure 21:
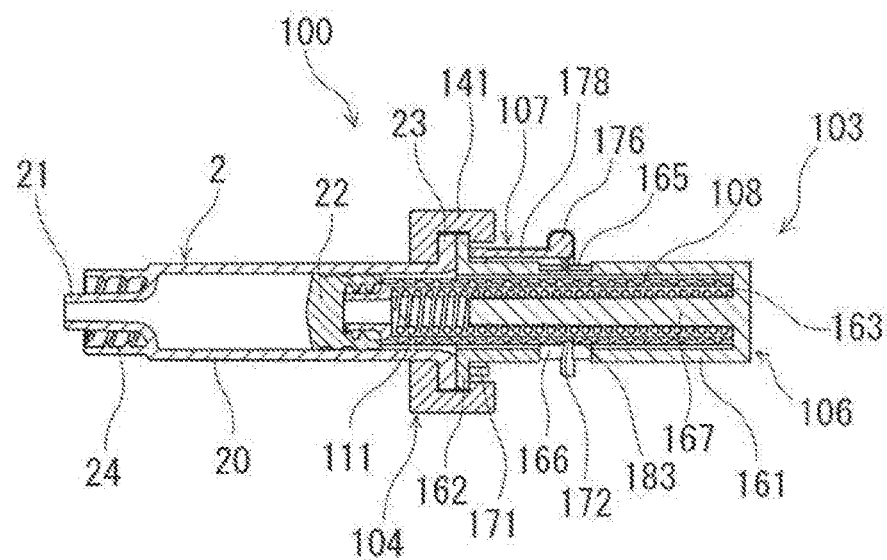
FIG. 21 is a cross-sectional view taken along line B-B of FIG. 16.
Figure 22:
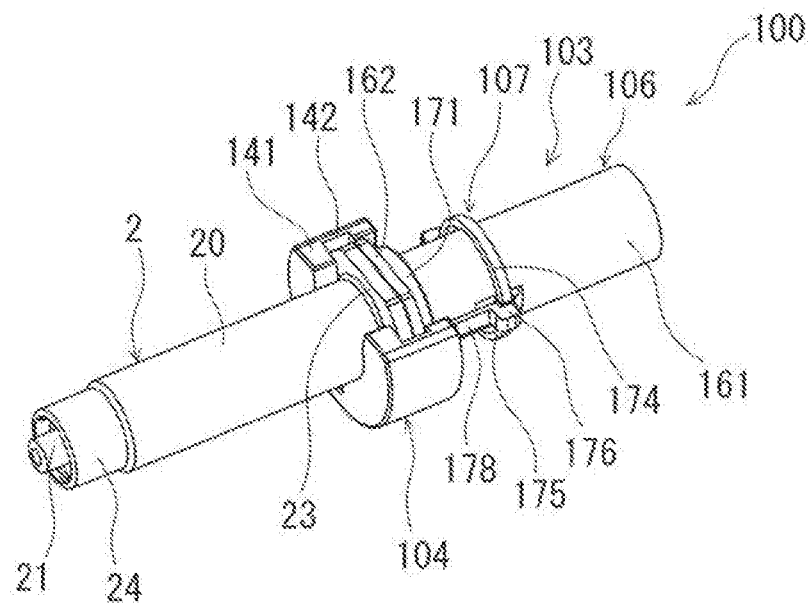
FIG. 22 is a perspective view of the medicine administration tool illustrated in FIG. 16 as seen obliquely from above.

As illustrated in FIG. 21, the biasing body pressing tubular member 106 is a member for pressing the pressing member biasing body 111 from the rear end side. As illustrated in FIGS. 21 and 24 to 26, a biasing body pressing tubular member 106 includes: a tubular main body portion 161; the flange portion 162 provided at the distal end portion of the main body portion 161; opening portions 165 and 166 through which the engagement protrusions 172 and 173 of the movement restriction member 107 enter, the opening portions 165 and 166 being provided at side portions that are more on the rear side than the flange portion 162; and a bar shaped portion 167 that protrudes in the distal end direction from the rear end inner surface (bottom surface portion 163) and can enter the inside of the pressing member biasing body 111.

The tubular main body portion 161 can accommodate the rear end portion of the pressing member biasing body 111. The bar shaped portion 167 enters into the pressing member biasing body 111, to restrict curving deformation of the pressing member biasing body 111 when the compressing (pressing) occurs in the pressing member biasing body 111.

As illustrated in FIGS. 20 to 28, in FIGS. 20 and 26 to 28 in particular, the movement restriction member 107 includes a ring-shaped distal end portion 171 held between the outer surface of the biasing body pressing tubular member 106 and the inner surface of the syringe attachment member 104; the engagement protrusions 172 and 173 that are positioned more on the rear side than the distal end portion 171 and provided in one end portion; the operation pressing portions 176 and 177; frames 174 and 175 that couple the engagement protrusions 172 and 173 and the operation pressing portions 176 and 177 to each other; and coupling portions 178 and 179 that connect each of the operation pressing portions 176 and 177 and the ring-shaped distal end portion 171.

Figure 28:
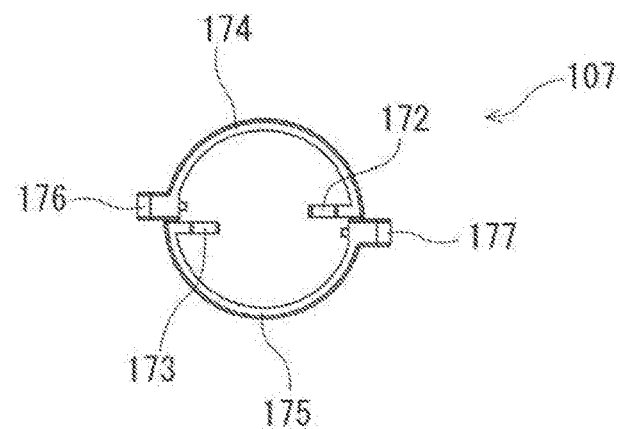
FIG. 28 is a right side view of the movement restriction member illustrated in FIG. 27.

The two coupling portions 178 and 179 of the movement restriction member 107 face each other and extend in a rear end direction from the rear end surface of the ring-shaped distal end portion 171. The operation pressing portions 176 and 177 are provided as bulging portions in the rear end portions of the coupling portions 178 and 179. As illustrated in FIGS. 26 and 28, the arc-shaped frames 174 and 175 extend from the operation pressing portions 176 and 177 and have distal end portions provided with protrusions that extend inward (direction toward the center of the movement restriction member 107). Distal end portions of the protrusions serve as engagement protrusions 172 and 173.

As illustrated in FIGS. 20 and 28, the engagement protrusions 172 and 173 substantially face the respective operation pressing portions 176 and 177 coupled thereto by the frames 174 and 175. In this embodiment, the movement restriction member 107 includes two independent operation units. The first operation unit includes the operation pressing portion 176, the engagement protrusion 172, the frame 174, and the coupling portion 178. The second operation unit includes the operation pressing portion 177, the engagement protrusion 173, the frame 175, and the coupling portion 179. Those components are connected to the ring-shaped distal end portion 171.

As illustrated in FIGS. 20, 21, and 23, the pressing portion biasing bodies 115 and 116 are each provided between the biasing body pressing tubular member 106 and a corresponding one of the operation pressing portions 176 and 177 of the movement restriction member 107. Preferably, a compressible coil spring is used as the pressing member biasing bodies 115 and 116, as illustrated in FIG. 20. The pressing member biasing bodies 115 and 116 may be a compressible tube-shaped elastic body. The operation pressing portions 176 and 177 are pressed outward by the pressing member biasing bodies 115 and 116. The engagement protrusions 172 and 173 coupled to the operation pressing portions 176 and 177 by the frames 174 and 175 are pressed inward, that is, against the outer surface of the gasket pressing member 108 as illustrated in FIGS. 20 and 23.

In this embodiment, the biasing body pressing tubular member 106 includes an accommodation portion that accommodates one end portions (lower end portions) of the pressing portion biasing bodies 115 and 116. In this embodiment, the accommodation portion is formed by step portions (recess portions) provided at side portions of the opening portions 165 and 166.

In the gasket pressing tool 103 of the present embodiment, as illustrated in FIG. 20, the engagement protrusions 172 and 173 provided through the opening portions 165 and 166 of the biasing body pressing tubular member 106 are pressed against the outer surface of the gasket pressing member 108, whereby the state where the gasket pressing member 108 and the pressing member-side engagement portion 183 are engaged is maintained. In the state illustrated in FIGS. 21 to 23 (i.e., normal state which is the non-operated state illustrated in FIG. 16 and FIG. 17), the engagement protrusions 172 and 173 each enter a gap between the two pressing member-side engagement portions 183, and the rear surface of the distal end portion of each of the engagement protrusions 172 and 173 comes into contact with the front surface of any of the pressing member-side engagement portions 183. With the engagement protrusions 172 and 173 and the pressing member-side engagement portion 183 engaged with each other, the movement of the gasket pressing member 108 biased by the pressing member biasing body 111 in the distal end direction is restricted.

Figure 29:
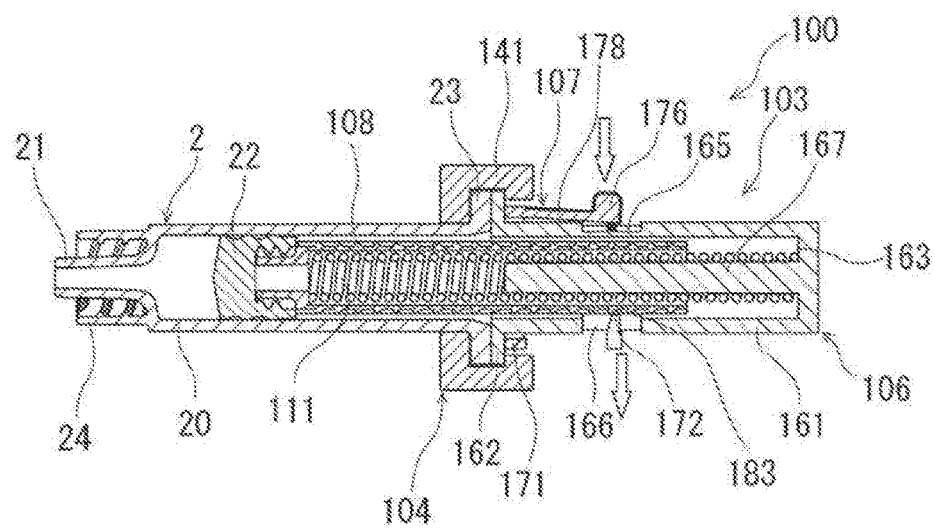
FIG. 29 is an explanatory diagram for explaining an operation of the medicine administration tool illustrated in FIG. 16.
Figure 30:
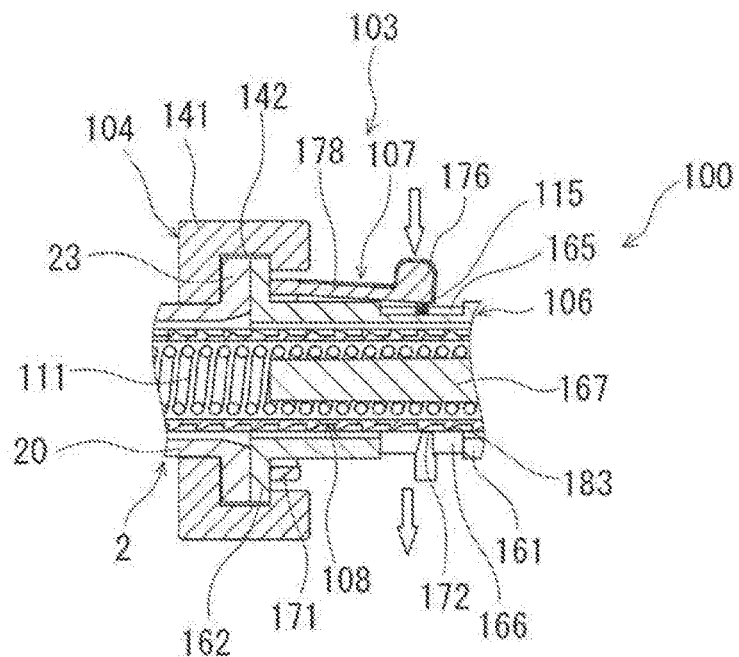
FIG. 30 is an explanatory diagram for explaining an operation of the medicine administration tool illustrated in FIG. 16.
Figure 31:
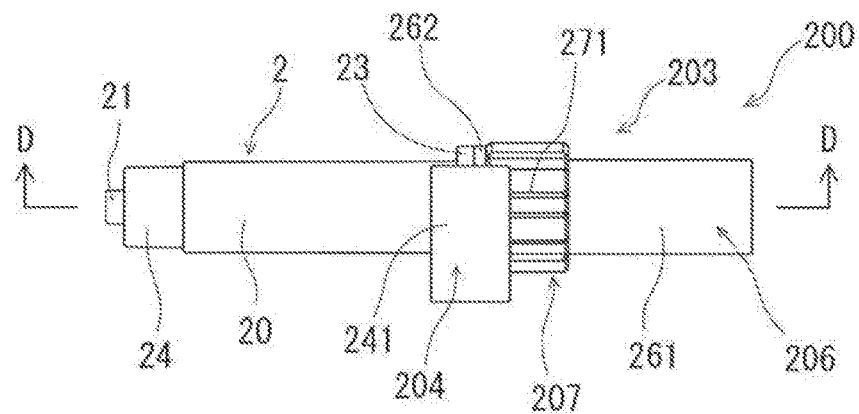
FIG. 31 is a front view of a medicine administration tool including a gasket pressing tool according to another embodiment.
Figure 32:
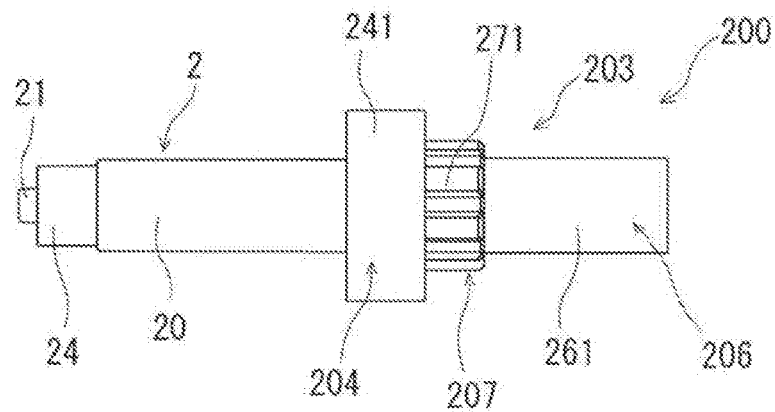
FIG. 32 is a bottom view of the medicine administration tool illustrated in FIG. 31.
Figure 33:
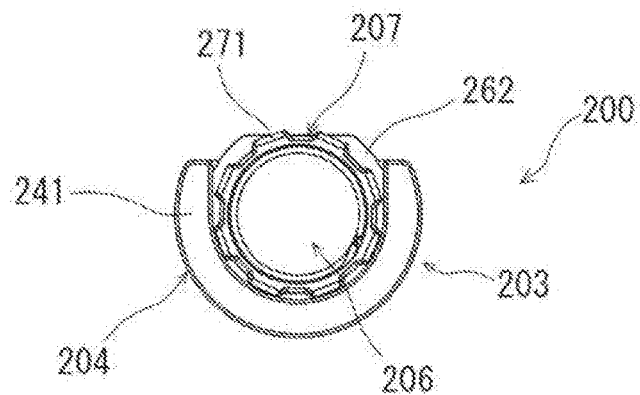
FIG. 33 is a right side view of the medicine administration tool illustrated in FIG. 31.

As illustrated in FIGS. 29 and 30, when the two operation pressing portions 176 and 177 of the movement restriction member 107 are simultaneously pressed in a direction indicated by an arrow, the engagement protrusions 172 and 173 move in the direction indicated by the arrows (outward) together with the frames, so that the engagement with the pressing member-side engagement portions 183 is released. Thus, the engagement between these components is released. Thus, with the pressing member biasing body 111, the gasket pressing member 108 presses the gasket 22 to move the gasket 22 in the distal end direction.

When the pressing of the operation pressing portions 176 and 177 stops, in the gasket pressing tool 103 of the present embodiment, the operation pressing portions 176 and 177 are immediately pushed up by the biasing bodies 115 and 116. Thus, the engagement protrusions 172 and 173 move together with the frames in a direction opposite to the direction indicated by the arrow in FIGS. 29 and 30 (inward). As a result, the engagement protrusions 172 and 173 engage again with the pressing member-side engagement portions 183, whereby the movement of the gasket pressing member 108 and the gasket 22 also stops.

Thus, with the gasket pressing tool 103 of this embodiment, the medicine can be administered only when the operation pressing portions 176 and 177 are pressed in the direction indicated by the arrow. Furthermore, the pressing member biasing body 111 assists the medicine administration.

Next, a medicine administration tool 200 and a gasket pressing tool 203 of an embodiment illustrated in FIGS. 31 to 41 will be described.

The medicine administration tool 200 of this embodiment includes: a syringe 2 including an outer tube 20 having a rear end portion provided with a flange 23 and a gasket 22 slidably accommodated in the outer tube 20; and the gasket pressing tool 203. As the syringe 2, a prefilled syringe 2a can be used. Furthermore, the medicine administration tool 200 may be in a state where the gasket pressing tool 203 is attached to the prefilled syringe 2a.

As illustrated in FIG. 31 to FIG. 41, the gasket pressing tool 203 of this embodiment has an operation function of releasing the engagement between an engagement protrusion 272 and the pressing member-side engagement portions 283, when the movement restriction member 207 is rotated as described later.

The movement restriction member 207 of the gasket pressing tool 203 of this embodiment includes a tubular portion 271 that partially encloses the distal end portion of the biasing body pressing tubular member 206 and an engagement protrusion 272 provided on the inner surface of the tubular portion 271. The gasket pressing tool 203 includes an annular biasing body 212 that is disposed between the biasing body pressing tubular member 206 and the movement restriction member 207, has one end portion fixed to the biasing body pressing tubular member 206, has the other end portion fixed to the movement restriction member 207, and maintains the state where the engagement protrusion 272 and the pressing member-side engagement portion 283 of the gasket pressing member 208 are engaged. These components achieve the engaged state maintaining function.

The gasket pressing tool 203 of this embodiment is configured in such a manner that when the movement restriction member 207 is rotated by a predetermined angle relative to the biasing body pressing tubular member 206, the engagement between the engagement protrusion 272 of the movement restriction member 207 and the pressing member-side engagement portion 283 of the gasket pressing member 208 is released, and that when the movement restriction member 207 is reversely rotated by the annular biasing body 212 in response to releasing of the rotation operation of the movement restriction member 207, the engagement protrusion 272 of the movement restriction member 207 and the pressing member-side engagement portion 283 of the gasket pressing member 208 engage with each other again.

Figure 37:
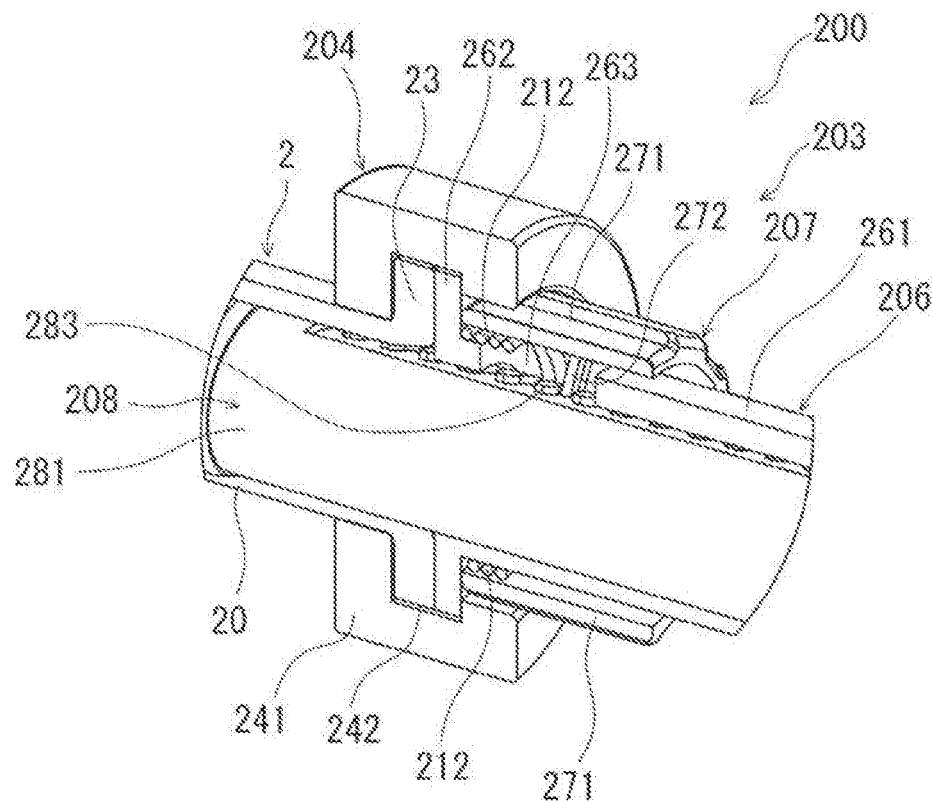
FIG. 37 is an enlarged view of the vicinity of a movement restriction member of the medicine administration tool illustrated in FIG. 36.
Figure 38:
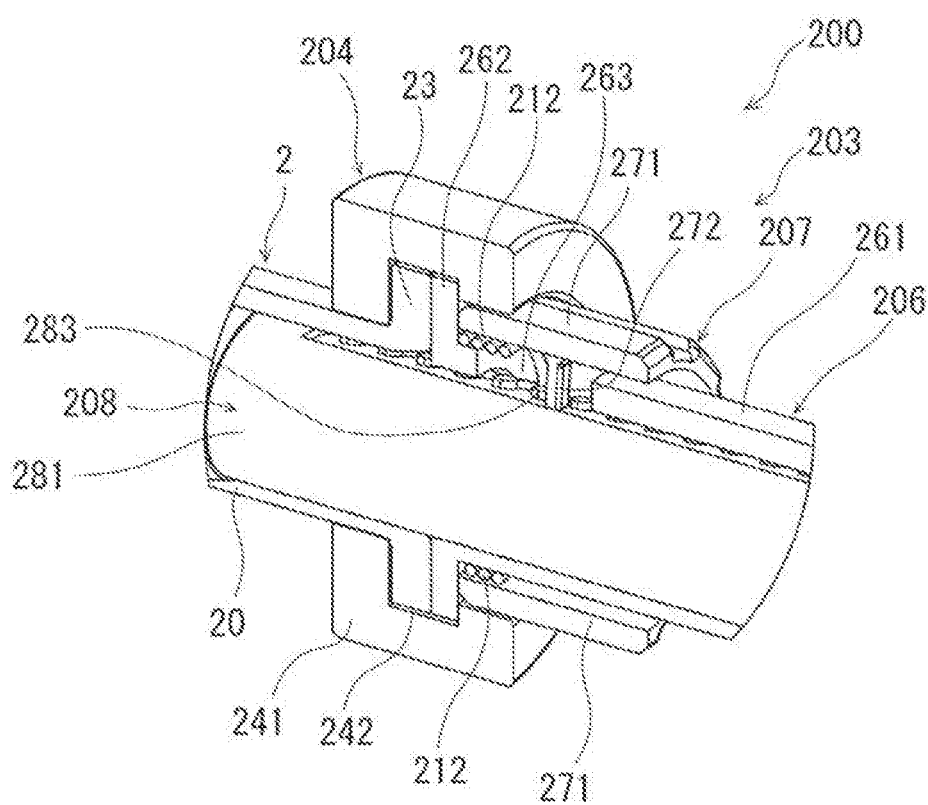
FIG. 38 is an explanatory diagram for explaining an operation of the medicine administration tool illustrated in FIG. 31.
Figure 39:
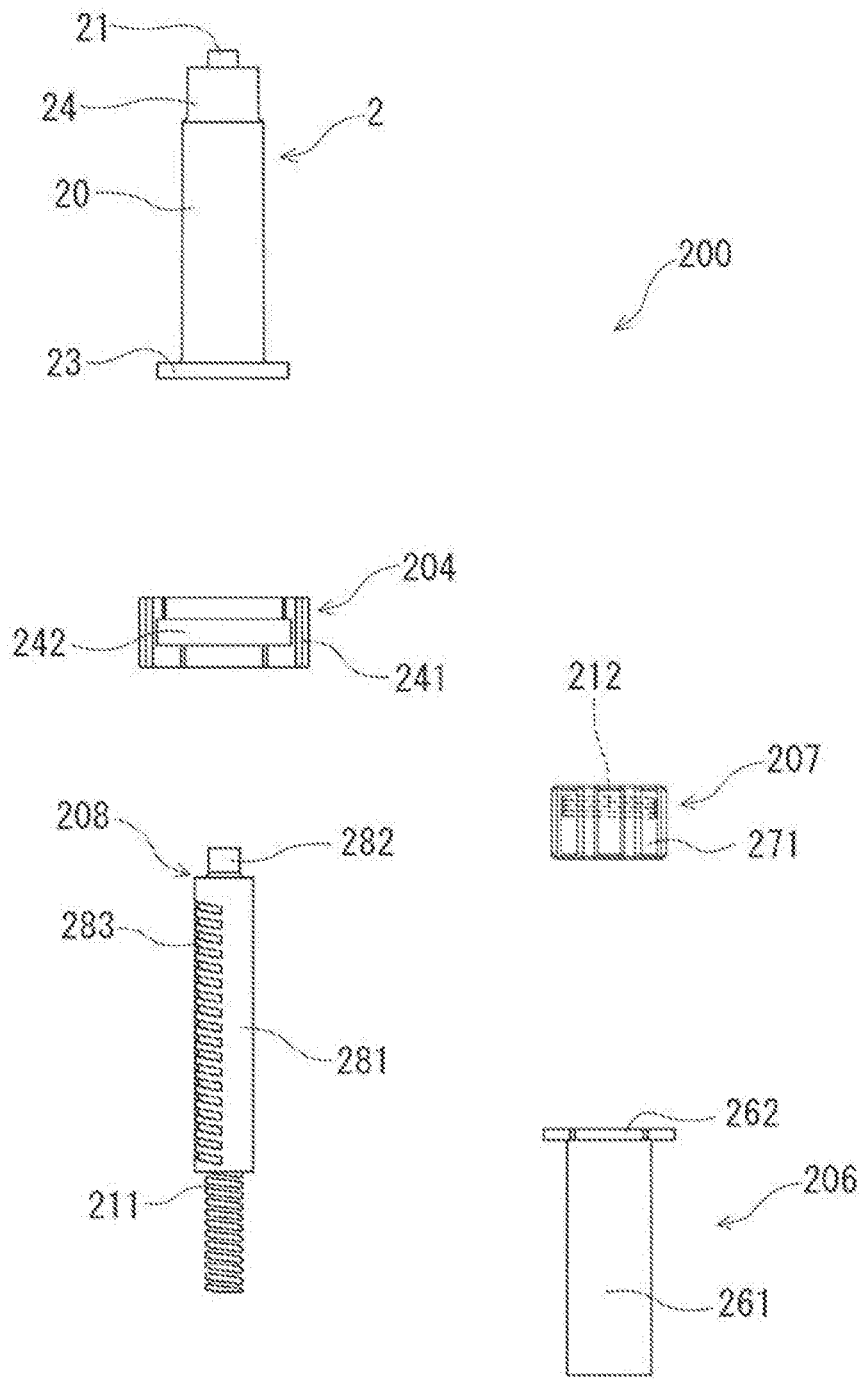
FIG. 39 is an explanatory diagram of components used in the medicine administration tool illustrated in FIG. 31.
Figure 40:
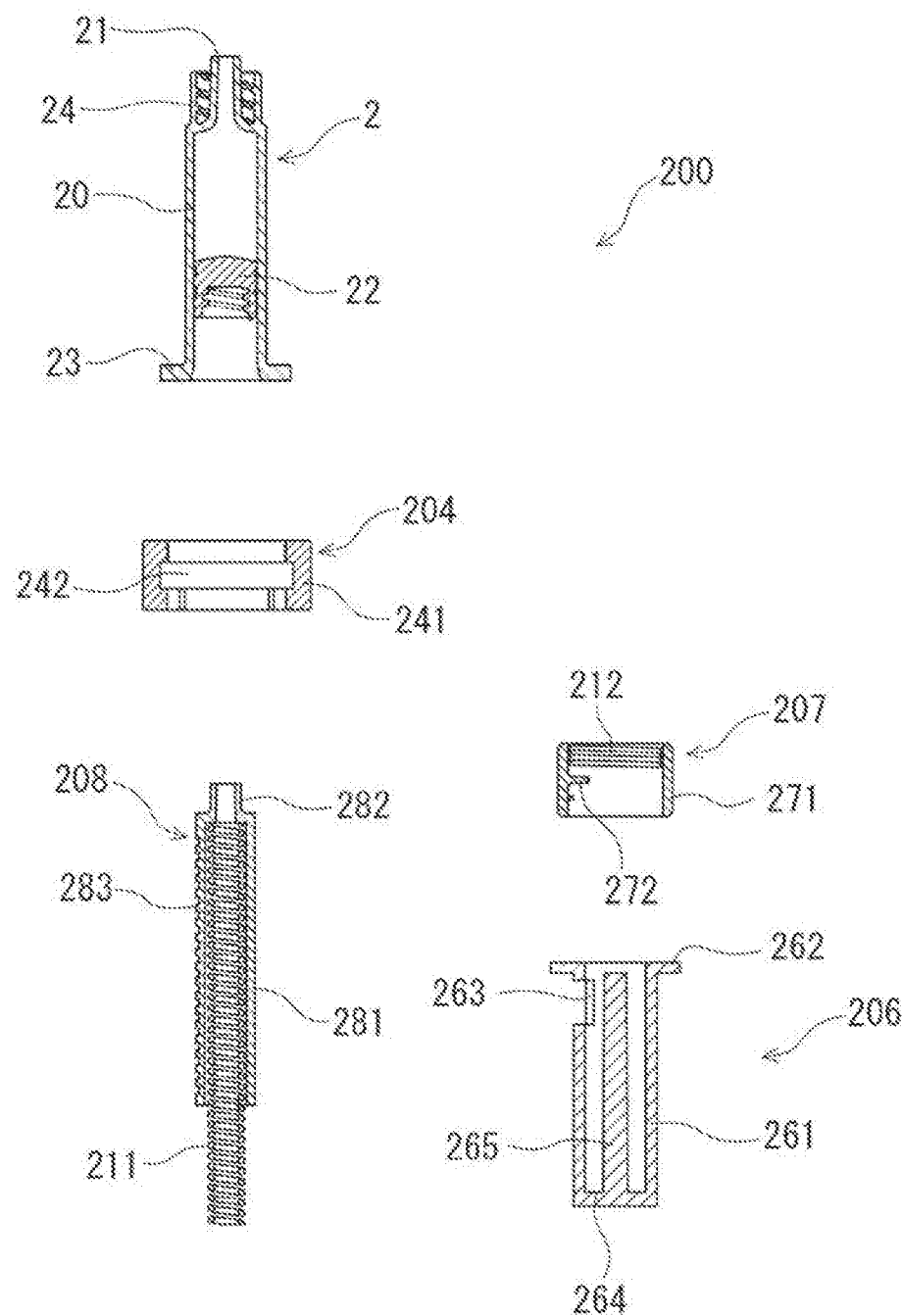
FIG. 40 is an explanatory diagram of components used in the medicine administration tool illustrated in FIG. 31.
Figure 41:
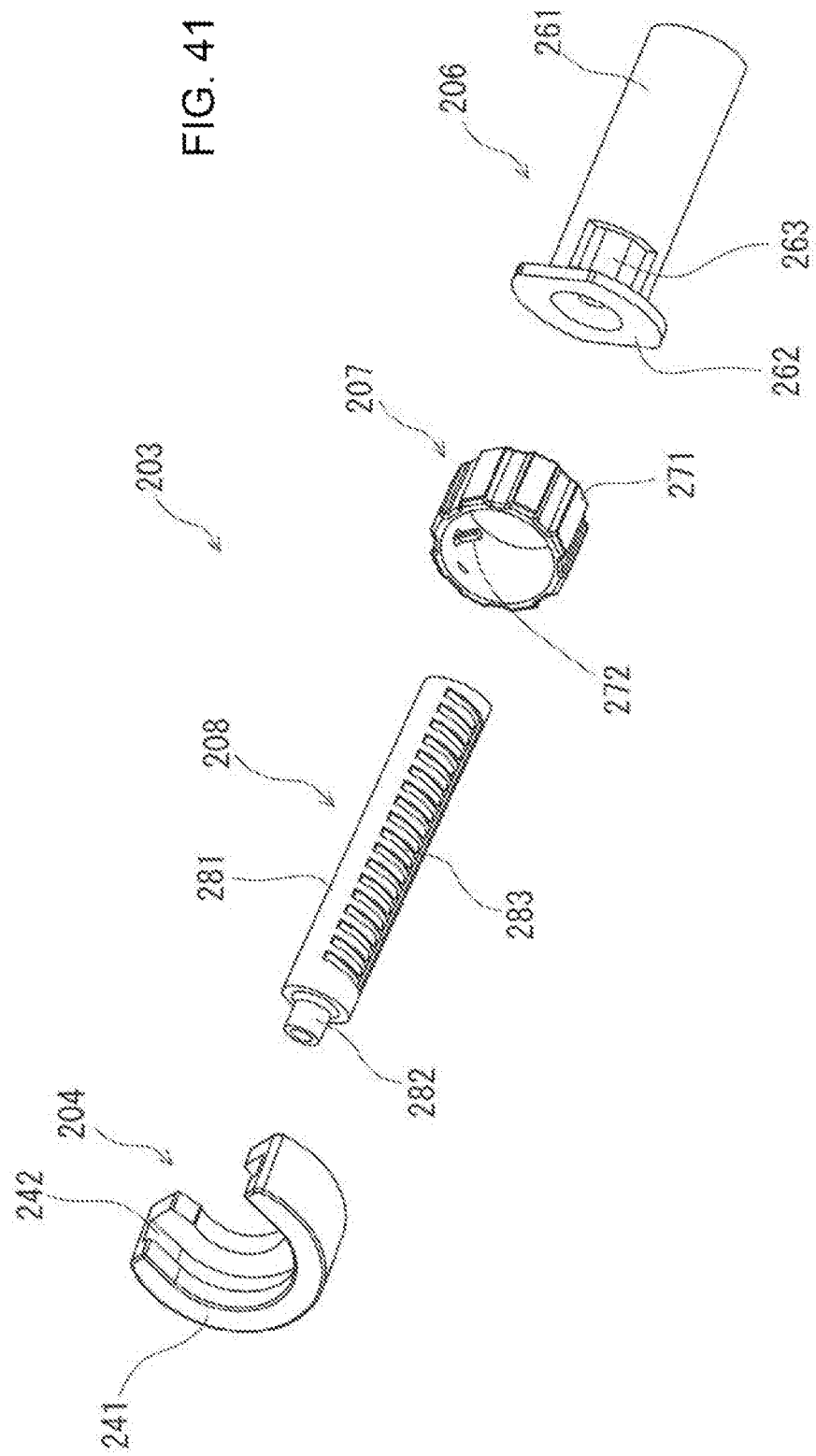
FIG. 41 is an explanatory view of components of the gasket pressing tool used in the medicine administration tool illustrated in FIG. 31.
Figure 42:
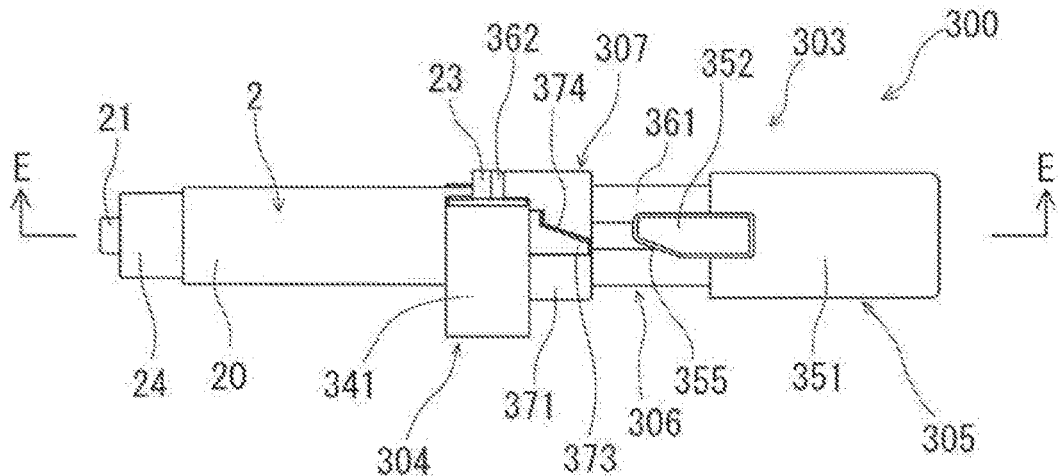
FIG. 42 is a front view of a medicine administration tool including a gasket pressing tool according to another embodiment.
Figure 43:
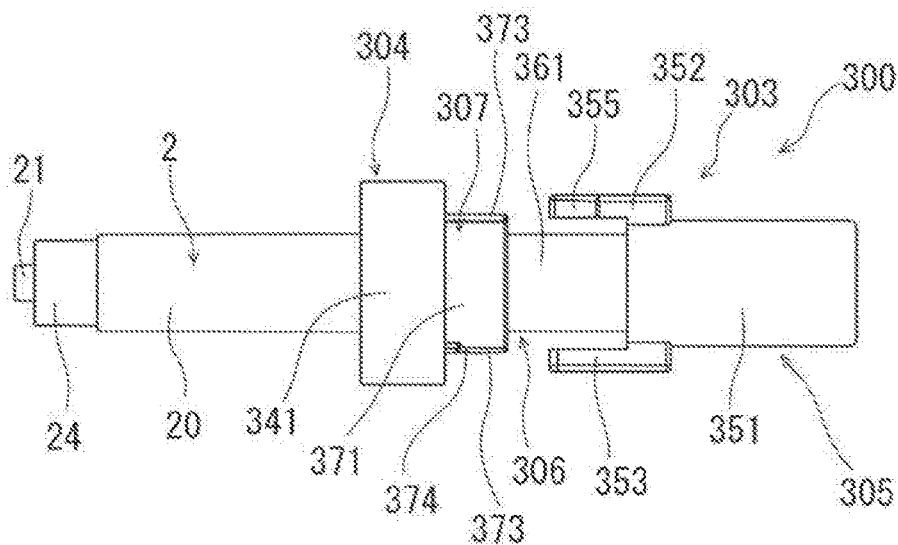
FIG. 43 is a bottom view of the medicine administration tool illustrated in FIG. 42.
Figure 44:
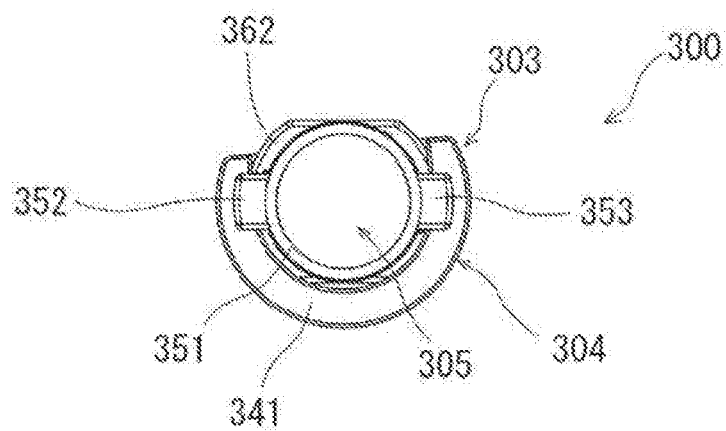
FIG. 44 is a right side view of the medicine administration tool illustrated in FIG. 42.
Figure 45:
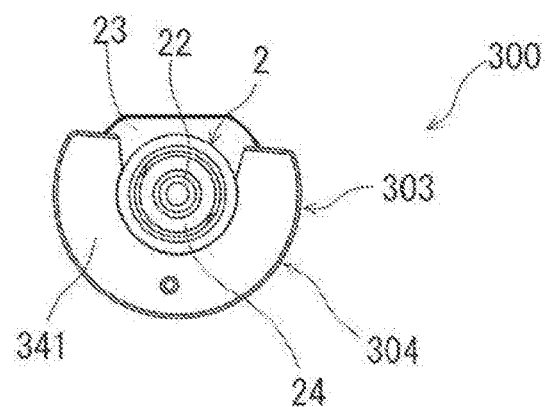
FIG. 45 is a left side view of the medicine administration tool illustrated in FIG. 42.

As illustrated in FIGS. 31 to 41, and in FIGS. 39 to 41 in particular, the gasket pressing tool 203 of this embodiment includes: a syringe attachment member 204; the tubular gasket pressing member 208; a pressing member biasing body 211 having a distal end side portion accommodated in the gasket pressing member 208; the biasing body pressing tubular member 206 that presses the pressing member biasing body 211 from the rear end side; and the movement restriction member 207.

As illustrated in FIGS. 31 to 41, the syringe attachment member 204 includes a main body portion 241 and an accommodation portion 242 formed by an arcuate recess portion extending downward from the upper surface of the main body portion 241. The accommodation portion 242 can accommodate the flange 23 of the outer tube 20 and a flange portion 262 of the biasing body pressing tubular member 206 at the same time. With these components thus accommodated, the gasket pressing tool 203 is attached (coupled) to the syringe 2 (outer tube 20). The syringe attachment member 204 can also be referred to as a syringe coupling member.

The gasket pressing member 208 is a tubular body having a tubular main body portion 281 as illustrated in FIGS. 34, 36, and 39 to 41. The distal end portion is provided with a distal end inner surface portion with which the distal end of the pressing member biasing body 211 accommodated can be in contact. The outer surface of the distal end portion is provided with an attachment portion 282 for the gasket. The outer surface of the tubular main body portion 281 is provided with a plurality of the pressing member-side engagement portions 283 that are arranged at an equal interval along the axial direction of the gasket pressing member 208 (tubular main body portion 281).

The gasket pressing member 208 has a distal end portion (specifically, the distal end surface of the tubular main body portion 281 or the gasket attachment portion 282) that can come into contact with the rear end portion of the gasket 22, and can press the gasket 22.

In this embodiment, the gasket pressing member 208 (tubular main body portion 281) includes a plurality of groove portions formed on the outer surface, with the front surfaces of the groove portions forming the pressing member-side engagement portions 283 that can come into contact (can engage) with the rear surface of the engagement protrusion 272. The groove portions form gaps into which the engagement protrusion 272 can enter in the circumferential direction, between the pressing member-side engagement portions 283 adjacent to each other in the axial direction. The pressing member-side engagement portions 283 may be formed by protruding portions.

Figure 34:
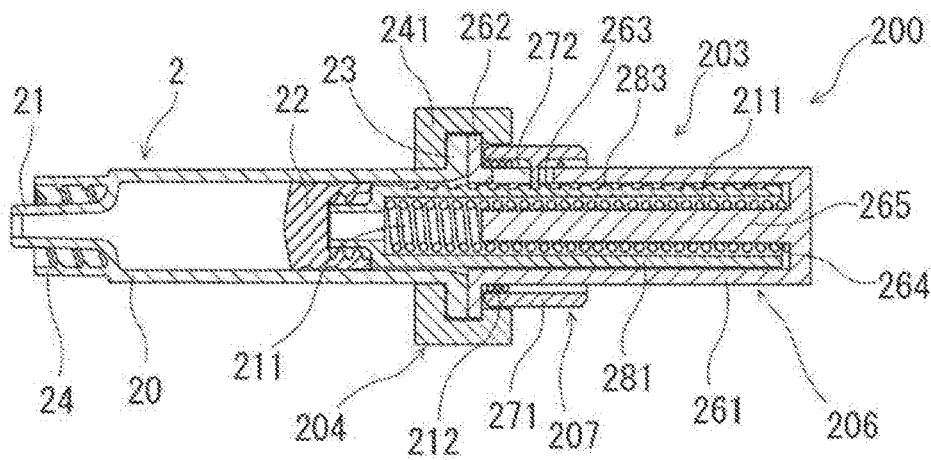
FIG. 34 is a cross-sectional view taken along line D-D of FIG. 31.
Figure 35:
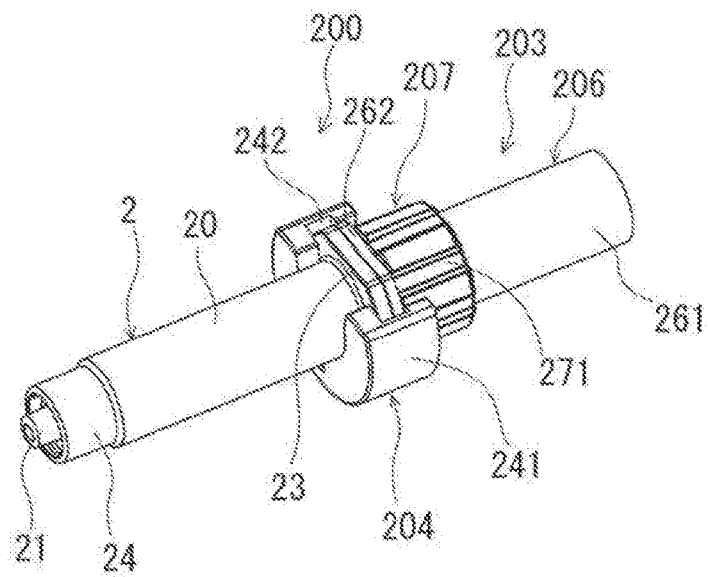
FIG. 35 is a perspective view of the medicine administration tool illustrated in FIG. 31 as seen obliquely from above.

Preferably, a compressible coil spring is used as the pressing member biasing body 211, as illustrated in FIGS. 34, 39, and 40. The pressing member biasing body 211 may be a compressible tube-shaped elastic body. The pressing member biasing body 211 is longer in length than the inner cavity of the tubular main body portion 281 of the gasket pressing member 208, has the distal end side accommodated in the gasket pressing member 208, and has a rear end portion that protrudes from the rear end of the gasket pressing member 208 in a state illustrated in FIGS. 34, 39, and 40, where the distal end surface is in contact with the distal end inner surface portion of the tubular main body portion 281.

As illustrated in FIG. 34, the biasing body pressing tubular member 206 is a member for pressing the pressing member biasing body 211 from the rear end side. As illustrated in FIGS. 34, 39, and 40, the biasing body pressing tubular member 206 includes: a tubular main body portion 261; a flange portion 262 provided at the distal end portion of the main body portion 261; an opening portion 263 through which the engagement protrusion 272 of the movement restriction member 207 described later enters, the opening portion 263 being provided at a side portion that is more on the rear side than the flange portion 262; and a bar shaped portion 265 that protrudes in the distal end direction from the rear end inner surface (bottom surface portion 264) and can enter the inside of the pressing member biasing body 211.

The tubular main body portion 261 can accommodate the rear end portion of the pressing member biasing body 211. The bar shaped portion 265 enters into the pressing member biasing body 211, to restrict curving deformation of the pressing member biasing body 211 when the compressing (pressing) occurs in the pressing member biasing body 211.

The movement restriction member 207 includes a tubular portion 271 that encloses the distal end portion of the biasing body pressing tubular member 206 and the engagement protrusion 272 provided on the inner surface of the tubular portion 271, as illustrated in FIGS. 31 to 41, in particular, in FIGS. 36, 37, and 39 to 41. Then, the engagement protrusion 272 enters through the opening portion 263 of the biasing body pressing tubular member 206, with the distal end of the engagement protrusion 272 entering through a gap near the outer surface of the gasket pressing member 208, specifically, a gap between the pressing member-side engagement portions 283, which are adjacent to each other, of the gasket pressing member 208. The rear surface of the engagement protrusion 272 engages with the front surface of the pressing member-side engagement portion 283, whereby the movement of the gasket pressing member 208 in the distal end direction is restricted.

This state where the movement of the gasket pressing member 208 in the distal end direction is restricted is maintained by the annular biasing body 212. Preferably, what is known as a torsion spring or a torsion coil spring is used as the annular biasing body 212. The torsion coil spring is a spring that receives a torsion moment around the center axis of the coil.

In the gasket pressing tool 203 of this embodiment, the torsion coil spring used as the annular biasing body 212 has one end portion fixed to the biasing body pressing tubular member 206, and has the other end portion fixed to the movement restriction member 207. Thus, the movement restriction member 207 is attached to the biasing body pressing tubular member 206 with the annular biasing body 212 interposed therebetween.

Figure 36:
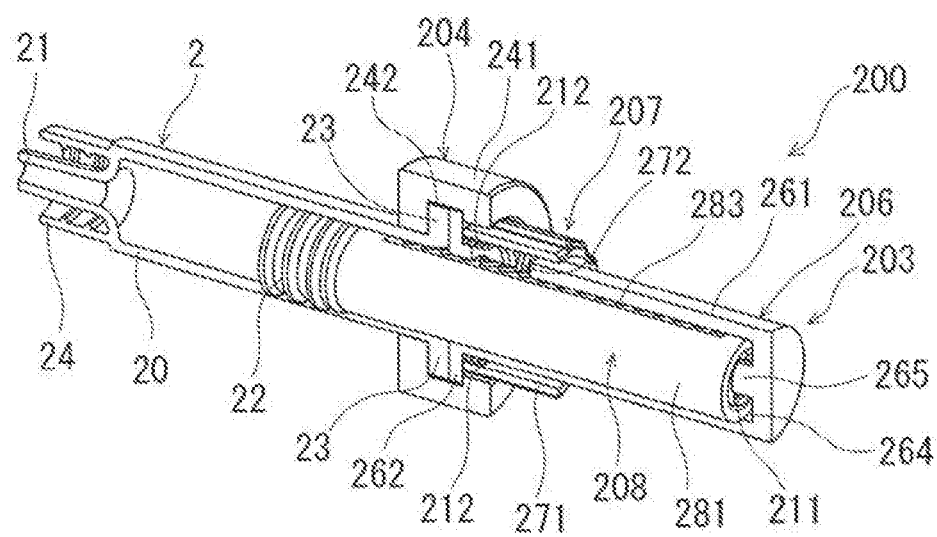
FIG. 36 is an explanatory diagram for explaining an internal structure of the medicine administration tool illustrated in FIG. 31.

In the gasket pressing tool 203 of this embodiment, in the normal state which is a state where the movement restriction member 207 is not operated, as illustrated in FIGS. 36 and 37, the annular biasing body 212 causes the distal end of the engagement protrusion 272 to move into a gap between the pressing member-side engagement portions 283, which are adjacent to each other, of the gasket pressing member 208, whereby the state where the movement of the gasket pressing member 208 in the distal end direction is restricted is maintained.

Furthermore, in the gasket pressing tool 203 of this embodiment, when the rotational force is applied to the movement restriction member 207 against the biasing force of the annular biasing body 212, the movement restriction member 207 rotates about the center axis of the movement restriction member 207 (biasing body pressing tubular member 206). When the movement restriction member 207 rotates, the engagement protrusion 272 of the movement restriction member 207 moves in the circumferential direction of the biasing body pressing tubular member 206, whereby the engagement between the engagement protrusion 272 and the pressing member-side engagement portion 283 is released.

Preferably, with the rotational operation of the movement restriction member 207, detachment of the engagement protrusion 272 from the gap between the adjacent pressing member-side engagement portions 283 in the circumferential direction is guaranteed. To this end, the pressing member-side engagement portion 283 appears in the engaged state, but does not extend to (not appear in) a direction of movement of the engagement protrusion 272 in the rotation of the movement restriction member 207.

As illustrated in FIG. 38, when the engagement between the engagement protrusion 272 and the pressing member-side engagement portion 283 is released by the operation of rotating the movement restriction member 207, the biasing body 212 causes the gasket pressing member 208 to press the gasket 22 and move the gasket 22 in the distal end direction.

In the gasket pressing tool 203 of this embodiment, when the rotation of the movement restriction member 207 stops, the annular biasing body 212 immediately causes the movement restriction member 207 to reversely rotate. Thus, the engagement protrusion 272 again engages with the pressing member-side engagement portion 283, and the movement of the gasket pressing member 208 and the gasket 22 stops.

Thus, with the gasket pressing tool 203 of this embodiment, the medicine can be administered only when the movement restriction member 207 is operated to rotate. Furthermore, the pressing member biasing body 211 assists the medicine administration.

Next, a medicine administration tool 300 and a gasket pressing tool 303 of an embodiment illustrated in FIGS. 42 to 55 will be described.

The medicine administration tool 300 of this embodiment includes: a syringe 2 including an outer tube 20 having a rear end portion provided with a flange 23 and a gasket 22 slidably accommodated in the outer tube 20; and the gasket pressing tool 303. As the syringe 2, a prefilled syringe 2a can be used. Furthermore, the medicine administration tool 300 may be in a state where the gasket pressing tool 303 is attached to the prefilled syringe 2a.

As illustrated in FIG. 42 to FIG. 55, the gasket pressing tool 303 of this embodiment has an operation function of releasing the engagement between an engagement protrusion 372 and a pressing member-side engagement portion 383, when the movement restriction member 307 is rotated with the operation member 305 being pressed (pushed) as described later.

The movement restriction member 307 of the gasket pressing tool 303 of this embodiment includes a tubular portion 371 that partially encloses the biasing body pressing tubular member 306 and an engagement protrusion 372 provided on the inner surface of the tubular portion 371. The gasket pressing tool 303 further includes an annular biasing body 312 that is disposed between the biasing body pressing tubular member 306 and the movement restriction member 307, has one end portion fixed to the biasing body pressing tubular member 306, has the other end portion fixed to the movement restriction member 307, and maintains the state where the engagement protrusion 372 and the pressing member-side engagement portion 383 of the movement restriction member 307 are engaged. These components achieve the engaged state maintaining function.

The gasket pressing tool 303 of this embodiment further includes a tubular operation member 305 that is attached to the rear end portion of the biasing body pressing tubular member 306, to be movable in the axial direction. The operation member 305 includes: a rotation protrusion portions 352 and 353 that come into contact with the movement restriction member 307 to rotate the movement restriction member 307 in a pushing operation toward the distal end side; and an operation member biasing body 313 that is accommodated in the operation member 305 and has a distal end coming into contact with the rear end surface of the biasing body pressing tubular member 306 to bias the operation member 305 rearward.

The gasket pressing tool 303 of this embodiment is configured in such a manner that when the movement restriction member 307 rotates with the operation member 305 pushed, the engagement between the engagement protrusion 372 of the movement restriction member 307 and the pressing member-side engagement portion 383 of the gasket pressing member 308 is released. When the pushing of the operation member 305 is released, the operation member 305 is retracted, and the annular biasing body 312 causes the reverse rotation of the movement restriction member, whereby the engagement protrusion 372 of the movement restriction member 307 and the pressing member-side engagement portion 383 of the gasket pressing member 308 are engaged with each other again.

Figure 52:
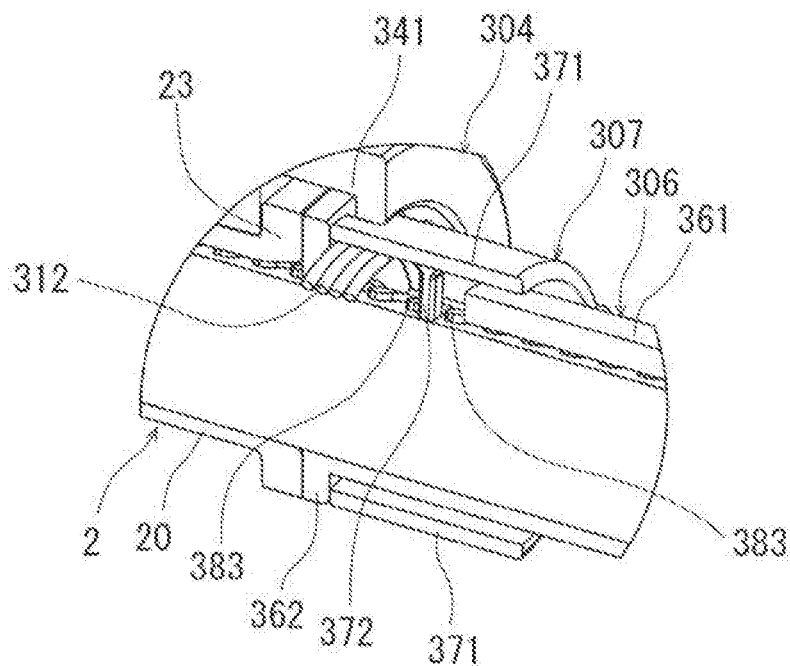
FIG. 52 is an enlarged view of the vicinity of a movement restriction member of the medicine administration tool illustrated in FIG. 51.
Figure 53:
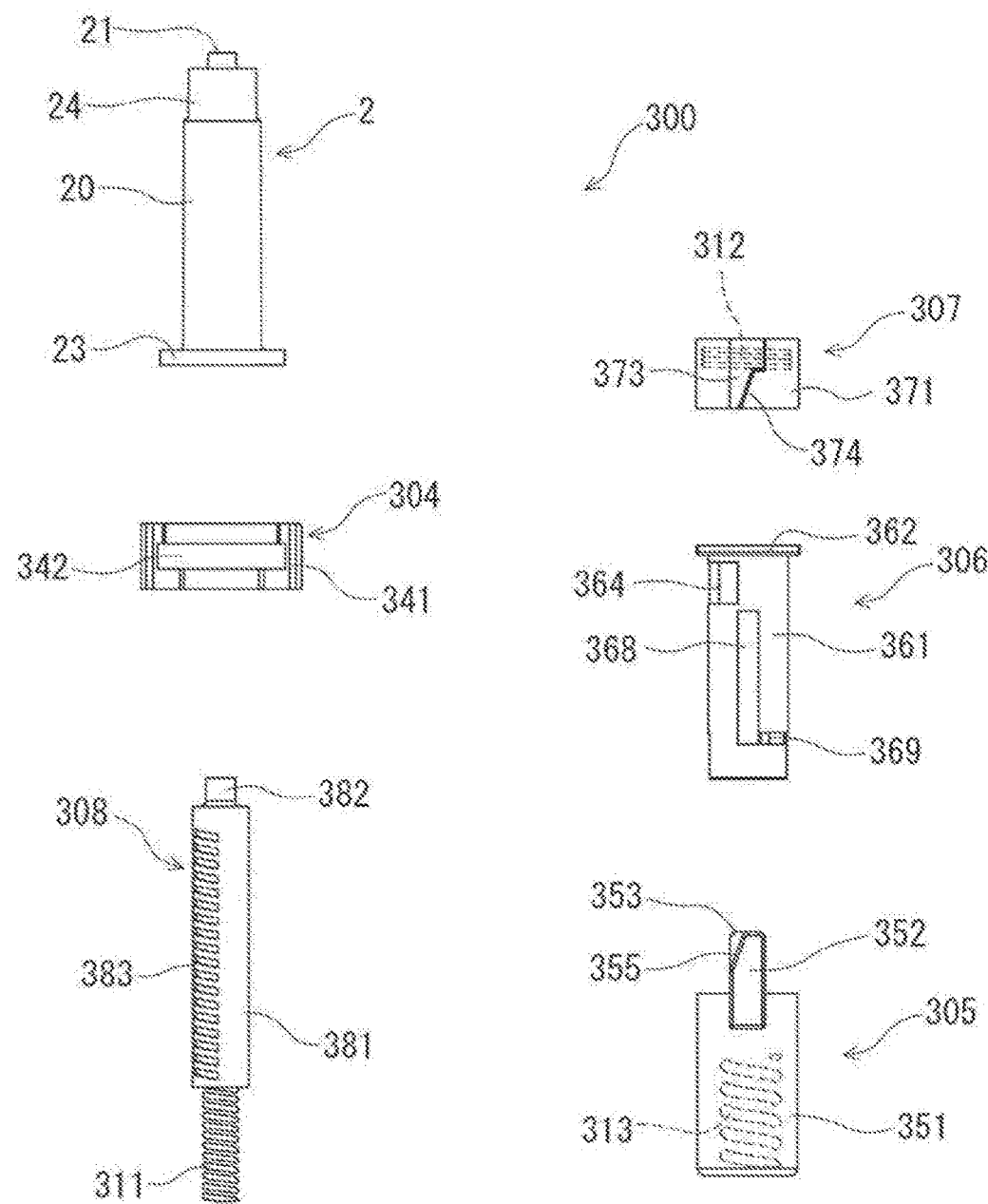
FIG. 53 is an explanatory diagram of components used in the medicine administration tool illustrated in FIG. 42.
Figure 54:
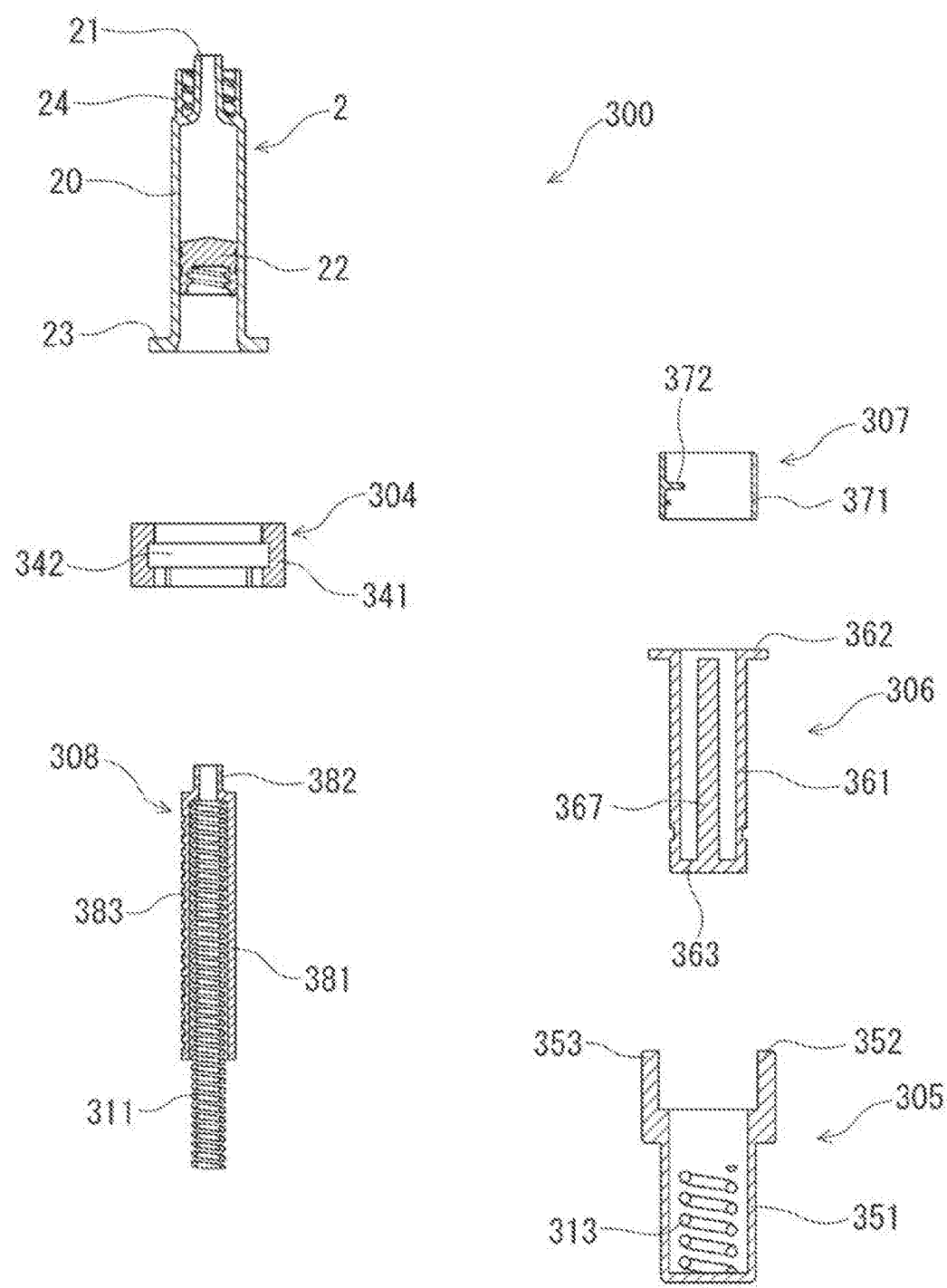
FIG. 54 is an explanatory diagram of components used in the medicine administration tool illustrated in FIG. 42.
Figure 55:
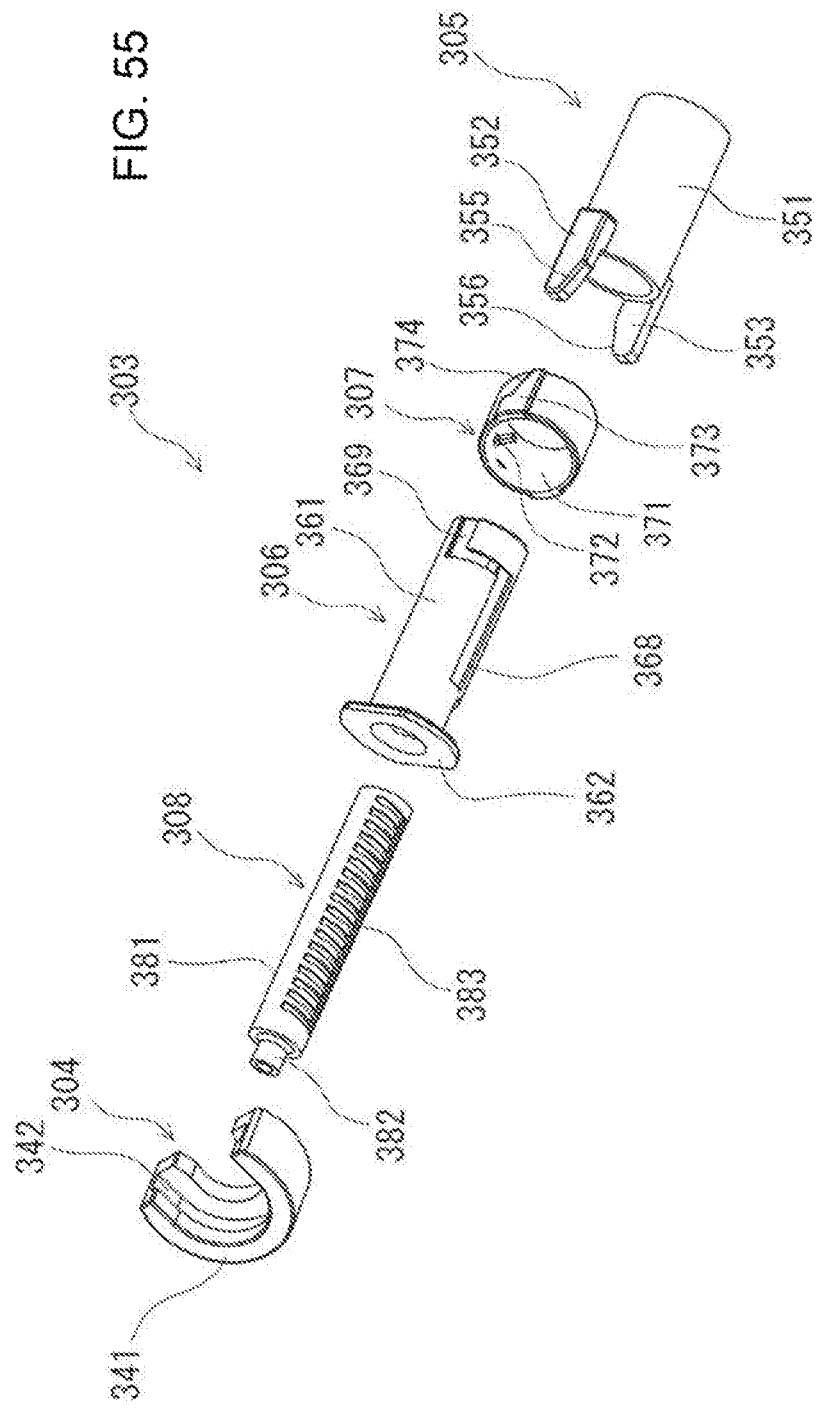
FIG. 55 is an explanatory view of components of the gasket pressing tool used in the medicine administration tool illustrated in FIG. 42.

As illustrated in FIGS. 42 to 55, and in FIGS. 53 to 55 in particular, the gasket pressing tool 303 of this embodiment includes: a syringe attachment member 304; the tubular gasket pressing member 308; a pressing member biasing body 311 having a distal end side portion accommodated in the gasket pressing member 308; the biasing body pressing tubular member 306 that presses the pressing member biasing body 311 from the rear end side; the movement restriction member 307; the operation member 305; and an operation member biasing body 313 that biases the operation member 305 rearward.

As illustrated in FIGS. 42 to 55, the syringe attachment member 304 includes a main body portion 341 and an accommodation portion 342 formed by an arcuate recess extending downward from the upper surface of the main body portion 341. The accommodation portion 342 can accommodate the flange 23 of the outer tube 20 and the flange portion 362 of the biasing body pressing tubular member 306 at the same time. With these components thus accommodated, the gasket pressing tool 303 is attached (coupled) to the syringe 2 (outer tube 20). The syringe attachment member 304 can also be referred to as a syringe coupling member.

The gasket pressing member 308 is a tubular body having a tubular main body portion 381 as illustrated in FIGS. 46 and 53 to 55. The distal end portion is provided with a distal end inner surface portion with which the distal end of the pressing member biasing body 311 accommodated can be in contact. The outer surface of the distal end portion is provided with an attachment portion 382 for the gasket. The outer surface of the tubular main body portion 381 is provided with a plurality of the pressing member-side engagement portions 383 that are arranged at an equal interval along the axial direction of the gasket pressing member 308 (tubular main body portion 381).

In this embodiment, the gasket pressing member 308 (tubular main body portion 381) includes a plurality of groove portions formed on the outer surface, with the front surfaces of the groove portions forming the pressing member-side engagement portions 383 that can come into contact (can engage) with the rear surface of the engagement protrusion 372. The groove portions form gaps into which the engagement protrusion 372 can enter in the circumferential direction, between the engagement portions 383 adjacent to each other in the axial direction. The pressing member-side engagement portions 383 may be formed by protruding portions.

The gasket pressing member 308 has a distal end portion (specifically, the distal end surface of the tubular main body portion 381 or the gasket attachment portion 382) that can engage with the rear end portion of the gasket 22, and can press the gasket 22.

Furthermore, the gasket pressing member 308 includes the plurality of pressing member-side engagement portions 383 adjacently arranged, as well as gaps into whi ch the engagement protrusions 372 can enter in the circumferential direction, the gaps each formed between the pressing member-side engagement portions 383 adjacent to each other in the axial direction.

Figure 46:
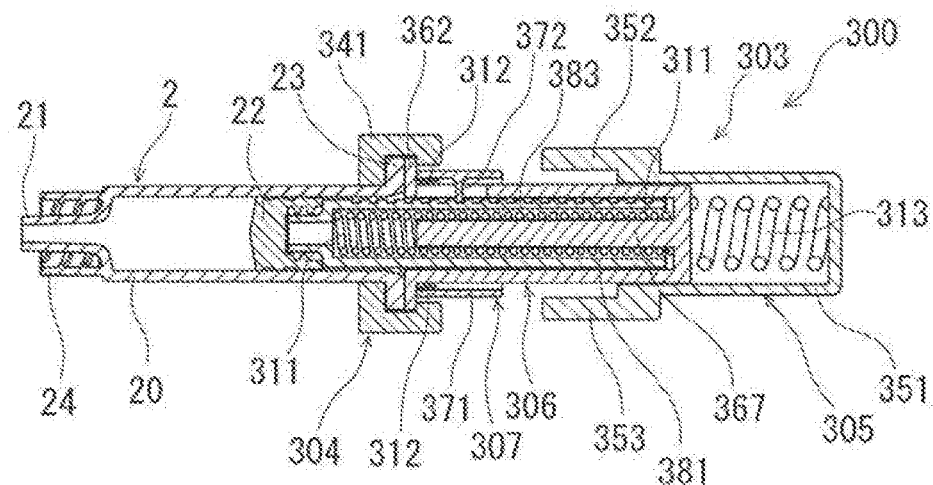
FIG. 46 is a cross-sectional view taken along line E-E of FIG. 42.
Figure 47:
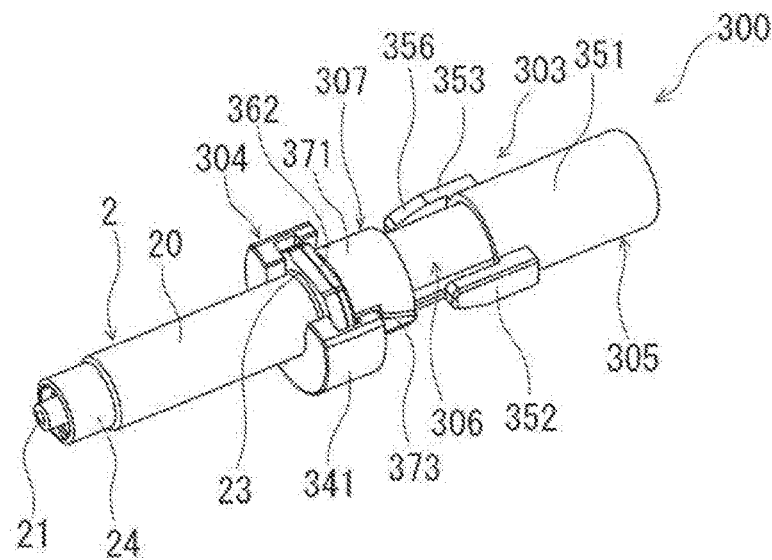
FIG. 47 is a perspective view of the medicine administration tool illustrated in FIG. 42 as seen obliquely from above.

Preferably, a compressible coil spring is used as the pressing member biasing body 311, as illustrated in FIGS. 46, 53, and 54. The pressing member biasing body 311 may be a compressible tube-shaped elastic body. The pressing member biasing body 311 is longer in length than the inner cavity of the tubular main body portion 381 of the gasket pressing member 308, has the distal end side accommodated in the gasket pressing member 308, and has a rear end portion that protrudes from the rear end of the gasket pressing member 308 in a state illustrated in FIGS. 46, 53, and 54, where the distal end surface is in contact with the distal end inner surface portion of the tubular main body portion 381.

As illustrated in FIG. 46, the biasing body pressing tubular member 306 is a member for pressing the pressing member biasing body 311 from the rear end side. As illustrated in FIGS. 46, 53, and 54, the biasing body pressing tubular member 306 includes: a tubular main body portion 361; a flange portion 362 provided at the distal end portion of the main body portion 361; an opening portion 364 through which the engagement protrusion 372 of the movement restriction member 307 described later enters, the opening portion 364 being provided at a side portion that is more on the rear side than the flange portion 362; and a bar shaped portion 367 that protrudes in the distal end direction from the rear end inner surface (bottom surface portion 363) and can enter the inside of the pressing member biasing body 311. The tubular main body portion 361 can accommodate the rear end portion of the pressing member biasing body 311. The bar shaped portion 367 enters into the pressing member biasing body 311, to restrict curving deformation of the pressing member biasing body 311 when the compressing (pressing) occurs in the pressing member biasing body 311.

Furthermore, as illustrated in FIGS. 53 and 55, the biasing body pressing tubular member 306 includes a guiding groove portion 369 including an axial direction recess portion 368, a circumferential groove portion extending in a circumferential direction from the rear end of the axial direction recess portion 368, and an axial direction groove portion extending in the axial direction from an end of the circumferential groove portion.

The movement restriction member 307 includes a tubular portion 371 that encloses the distal end portion of the biasing body pressing tubular member 306 and an engagement protrusion 372 provided on the inner surface of the tubular portion 371, as illustrated in FIGS. 42 to 55, in particular, in FIGS. 48, 49, and 53 to 55. The engagement protrusion 372 enters through the opening portion 364 of the biasing body pressing tubular member 306, with the distal end of the engagement protrusion 372 entering through a gap near the outer surface of the gasket pressing member 308, specifically, a gap between the pressing member-side engagement portions 383, which are adjacent to each other, of the gasket pressing member 308. The rear surface of the engagement protrusion 372 engages with the front surface of the pressing member-side engagement portion 383, whereby the movement of the gasket pressing member 308 in the distal end direction is restricted.

This state where the movement of the gasket pressing member 308 in the distal end direction is restricted is maintained by the annular biasing body 312. Preferably, what is known as a torsion spring or a torsion coil spring is used as the annular biasing body 312. The torsion coil spring is a spring that receives a torsion moment around the center axis of the coil.

In the gasket pressing tool 303 of this embodiment, the torsion coil spring used as the annular biasing body 312 has one end portion fixed to the biasing body pressing tubular member 306, and has the other end portion fixed to the movement restriction member 307. Thus, the movement restriction member 307 is fixed to the biasing body pressing tubular member 306 with the annular biasing body 312 interposed therebetween.

As illustrated in FIGS. 42 to 55, and in FIGS. 46, 48, 51, and 53 to 55, in particular, the operation member 305 includes: a tubular main body portion 351; the rotation protrusion portions 352 and 353 provided on the outer surface of the distal end portion of the main body portion 351; and a sliding protrusion provided on the inner surface of the distal end portion of the tubular main body portion 351 that is the inner side of the rotation protrusion portions 352 and 353.

The sliding protrusion enters into the axial direction recess portion 368 of the biasing body pressing tubular member 306 to enable the operation member 305 to be slidable in the axial direction of the biasing body pressing tubular member 6, and guides the rotation protrusion portions 352 and 353 of the operation member 305 to the outer surface of the tubular portion 371 of the movement restriction member 307. The sliding protrusion is inserted from the rear end of the axial direction groove portion of the guiding groove portion 369 of the biasing body pressing tubular member 306. When the operation member 305 is rotated after the sliding protrusion reaches the circumferential groove portion, the sliding protrusion can enter the axial direction recess portion 368. Furthermore, the circumferential groove portion of the guiding groove portion 369 is provided with a retaining rib.

As illustrated in FIGS. 42, 47, 53, and 55, the movement restriction member 307 of the gasket pressing tool 303 of this embodiment includes an enclosed member-side inclined portion 374 that is provided on the outer surface of the movement restriction member 307 and is formed to be inclined in a rotation direction in which the engagement between the engagement protrusion 372 and the pressing member-side engagement portion 383 is released. In this embodiment, the movement restriction member 307 includes an outer surface raised portion 373 the side wall of which forming the enclosed member-side inclined portion 374. The enclosed member-side inclined portion 374 may be formed by an inner side surface of a recess portion provided in the movement restriction member 307.

The operation member 305 includes operation member side inclined portions 355 and 356 provided on the rotation protrusion portions 352 and 353, as illustrated in FIGS. 46, 48, 51, and 53 to 55. When the pushing operation is performed on the operation member 305, the operation member side inclined portions 355 and 356 come into sliding contact with the enclosed member-side inclined portions 374 to rotate the movement restriction member 307.

As illustrated in FIGS. 46, 48, and 53 and 54, the operation member biasing body 313 is accommodated in the operation member 305 (in the tubular main body portion 351). A compressible coil spring is preferably used as the operation member biasing body 313. The pressing member biasing body 313 may be a compressible tube-shaped elastic body. As illustrated in FIG. 46, the operation member biasing body 313 has a distal end that comes into contact with the rear end outer surface of the biasing body pressing tubular member 306, has a rear end that comes into contact with the rear end inner surface of the operation member 305, and can be pressed by these surfaces. The compressed operation member biasing body 313 presses (biases) the operation member 305 rearward.

In the gasket pressing tool 303 of this embodiment, two enclosed member-side inclined portions 374 of the movement restriction member 307 are provided to face each other and two rotation protrusion portions 352 and 353 of the operation member 305 are provided to face each other, respectively.

Figure 48:
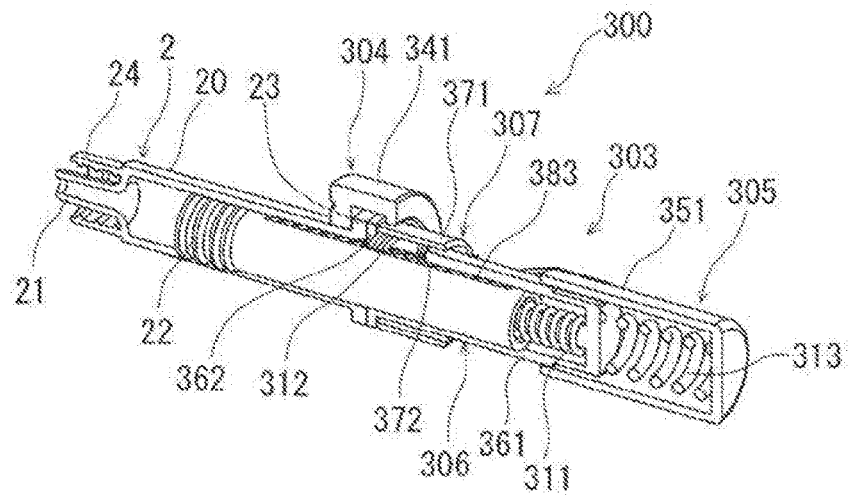
FIG. 48 is an explanatory diagram for explaining an internal structure of the medicine administration tool illustrated in FIG. 42.
Figure 49:
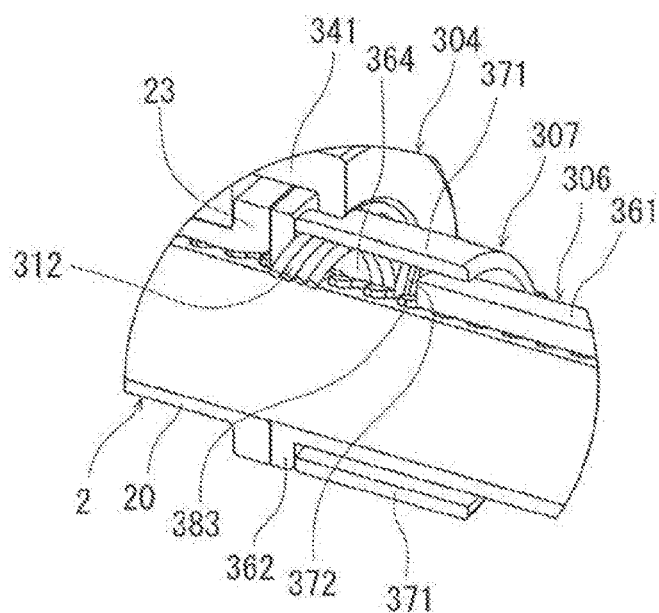
FIG. 49 is an enlarged view of the vicinity of a movement restriction member of the medicine administration tool illustrated in FIG. 48.

In the gasket pressing tool 303 of this embodiment, in the normal state which is a state where the operation member 305 is not operated (a state where the movement restriction member 307 is not rotated), as illustrated in FIGS. 48 and 49, the annular biasing body 312 causes the distal end of the engagement protrusion 372 to move into a gap between the pressing member-side engagement portions 383, which are adjacent to each other, of the gasket pressing member 308, whereby the state where the movement of the gasket pressing member 308 in the distal end direction is restricted is maintained.

Figure 50:
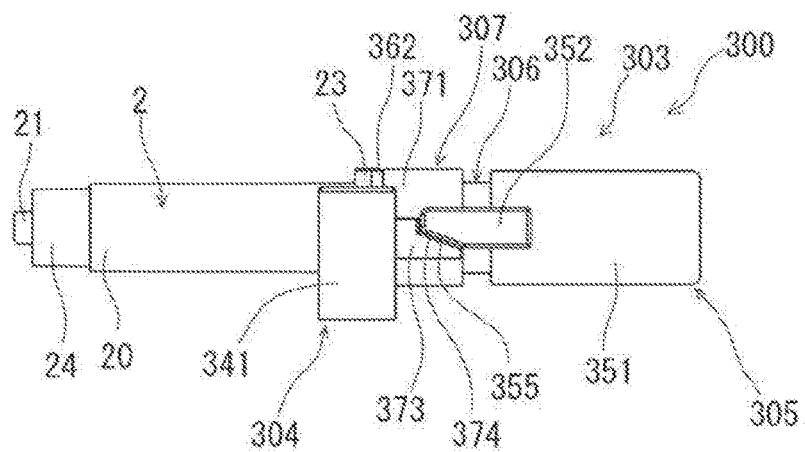
FIG. 50 is an explanatory diagram for explaining an operation of the medicine administration tool illustrated in FIG. 42.
Figure 51:
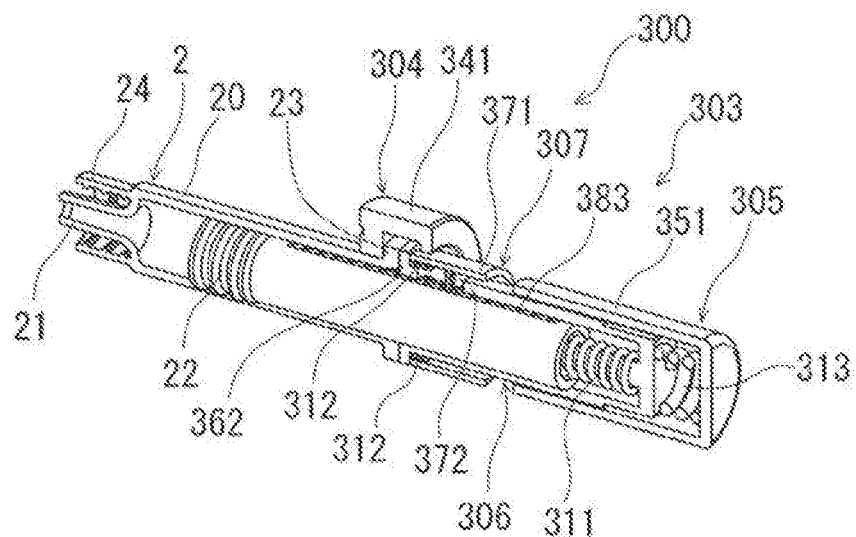
FIG. 51 is an explanatory diagram for explaining an operation of the medicine administration tool illustrated in FIG. 42.

In the gasket pressing tool 303 of this embodiment, as illustrated in FIG. 50, when the operation member 305 is pressed and pushed in, as illustrated in FIGS. 50 and 51, the operation member 305 moves forward and the rotation protrusion portions 352 and 353 of the operation member 305 come into sliding contact with the enclosed member-side inclined portions 374 of the movement restriction member 307, whereby the rotational force against the biasing force of the annular biasing body 312 is applied to the movement restriction member 307.

As a result, as illustrated in FIGS. 51 and 52, the movement restriction member 307 rotates about the center axis of the movement restriction member 307 (the biasing body pressing tubular member 306). When the movement restriction member 307 rotates, the engagement protrusion 372 of the movement restriction member 307 moves in the circumferential direction of the biasing body pressing tubular member 306, whereby the engagement between the engagement protrusion 372 and the pressing member-side engagement portion 383 is released.

Preferably, with the rotational operation of the movement restriction member 307, detachment of the engagement protrusion 372 from the gap between the adjacent pressing member-side engagement portions 383 in the circumferential direction is guaranteed. To this end, the pressing member-side engagement portion 383 appears in the engaged state, but does not extend to (not appear in) a movement direction of the engagement protrusion 372 when the movement restriction member 307 rotates.

As illustrated in FIGS. 51 and 52, when the engagement between the engagement protrusion 372 and the pressing member-side engagement portion 383 is released by the rotation operation of the movement restriction member 307, the biasing body 312 causes the gasket pressing member 308 to press the gasket 22 and move the gasket 22 in the distal end direction.

In the gasket pressing tool 303 of this embodiment, when pressing of the operation member 305 stops, the operation member 305 is moved by the biasing body 313, and the biasing body 312 immediately causes the reverse rotation of the movement restriction member 307. Thus, the engagement protrusion 372 again engages with the pressing member-side engagement portion 383, and the movement of the gasket pressing member 308 and the gasket 22 stops.

Thus, with the gasket pressing tool 303 of this embodiment, the medicine can be administered only when the pushing operation is performed on the operation member 305. Furthermore, the pressing member biasing body 311 assists the medicine administration.

INDUSTRIAL APPLICABILITY

The gasket pressing tool is as follows.

(1) A gasket pressing tool to move a gasket of a syringe including an outer tube and the gasket in a distal end direction, the outer tube having a rear end portion provided with a flange, the gasket being slidably accommodated in the outer tube, the gasket pressing tool including:

a gasket pressing member capable of pressing the gasket in the distal end direction;

a syringe attachment member attached to the flange of the outer tube;

a pressing member biasing body having a distal end portion accommodated in the gasket pressing member and having a rear end portion protruding from the gasket pressing member;

a biasing body pressing tubular member that accommodates the rear end portion of the pressing member biasing body and has a flange portion that is provided at a distal end portion and is accommodated in the syringe attachment member and an opening portion that is provided at a side portion more on a rear side than the flange portion; and a movement restriction member that is held by the biasing body pressing tubular member and/or the syringe attachment member, includes an engagement protrusion that enters into the biasing body pressing tubular member through the opening portion, and restricts a movement of the gasket pressing member, wherein the gasket pressing member includes a plurality of pressing member-side engagement portions arranged in an axial direction, the pressing member-side engagement portions being capable of engaging with the engagement protrusion of the movement restriction member, and the gasket pressing tool further has an engaged state maintaining function of maintaining a state of engagement between the engagement protrusion of the movement restriction member and the pressing member-side engagement portions of the gasket pressing member, and an engagement protrusion operation function of moving the engagement protrusion to release the engagement between the engagement protrusion and the pressing member-side engagement portion.

The gasket pressing tool moves the gasket of the syringe including the outer tube having the rear end portion provided with the flange and the gasket slidably accommodated in the outer tube in the distal end direction. The gasket pressing tool includes a gasket pressing member capable of pressing the gasket in the distal end direction, a syringe attachment member attached to the flange of the outer tube, a pressing member biasing body having a distal end portion accommodated in the gasket pressing member and having a rear end portion protruding from the gasket pressing member, a biasing body pressing tubular member that accommodates the rear end portion of the pressing member biasing body and has a flange portion that is provided at a distal end portion and is accommodated in the syringe attachment member and an opening portion that is provided at a side portion more on a rear side than the flange portion, and a movement restriction member that is held by the biasing body pressing tubular member and/or the syringe attachment member, includes an engagement protrusion that enters into the biasing body pressing tubular member through the opening portion, and restricts a movement of the gasket pressing member, and the gasket pressing member includes a plurality of pressing member-side engagement portions arranged in an axial direction, the pressing member-side engagement portions being capable of engaging with the engagement protrusion of the movement restriction member, and the gasket pressing tool further has an engaged state maintaining function of maintaining a state of engagement between the engagement protrusion of the movement restriction member and the pressing member-side engagement portions of the gasket pressing member, and an engagement protrusion operation function of moving the engagement protrusion to release the engagement between the engagement protrusion and the pressing member-side engagement portion.

In the gasket pressing tool in a normal state, the engagement protrusion of the operation member is engaged with the pressing member-side engagement portions due to the engaged state maintaining function, and thus the forward movement of the gasket pressing member is restricted. When the engagement between the engagement protrusion of the operation member and the pressing member-side engagement portions is released due to the engagement protrusion operation function, the gasket pressing member is pressed in the distal end direction by the pressing member biasing body. Thus, with the gasket pressed by the biasing force of the pressing member biasing body, the movement of the gasket is favorably assisted and medicine can be easily discharged. When the engagement releasing by the engagement protrusion operation function ends, the engagement protrusion of the operation member and the pressing member-side engagement portions are engaged with each other again due to the engaged state maintaining function, whereby the forward movement of the gasket pressing member is restricted. Thus, the medicine discharge can be easily interrupted or stopped, and a predetermined amount of medicine can be easily discharged.

Further, the above embodiment may be as follows.

(2) The gasket pressing tool according to (1) described above, wherein the movement restriction member includes a restriction member main body portion that has a distal end portion held by the biasing body pressing tubular member, extends rearward from the distal end portion, and is elastically deformable, and the engagement protrusion extending in a direction toward the gasket pressing member from the main body portion, and the engaged state maintaining function is achieved with the restriction member main body portion pressing the engagement protrusion in a direction toward the pressing member-side engagement portions of the gasket pressing member.

(3) The gasket pressing tool according to (1) or (2) described above, wherein the gasket pressing tool has the engagement protrusion operation function with the gasket pressing tool including a tubular operation member that is attached to a rear end portion of the biasing body pressing tubular member to be movable in the axial direction and an operation member biasing body that is accommodated in the operation member, has a distal end coming into contact with a rear end surface of the biasing body pressing tubular member, and biases the operation member rearward, and with the operation member including an engagement releasing protrusion portion that comes into contact with and pushes up the movement restriction member in moving toward a distal end side, to release the engagement between the engagement protrusion and the pressing member-side engagement portions.

(4) The gasket pressing tool according to (1) described above, wherein the opening portion of the biasing body pressing tubular member and the engagement protrusion of the movement restriction member include two opening portions facing each other and two engagement protrusions facing each other, respectively.

(5) The gasket pressing tool according to (3) described above, wherein the opening portion of the biasing body pressing tubular member, the engagement protrusion of the movement restriction member, and the engagement releasing protrusion portion of the operation member include two opening portions facing each other, two engagement protrusions facing each other, and two engagement releasing protrusion portions facing each other, respectively.

(6) The gasket pressing tool according to (1) described above, wherein the gasket pressing tool has the engaged state maintaining function with the movement restriction member including an operation unit that includes a distal end portion held by the biasing body pressing tubular member and/or the syringe attachment member, the engagement protrusion that is provided more on the rear side than the distal end portion and is provided in one end portion, an operation pressing portion, and a frame coupling the engagement protrusion and the operation pressing portion to each other, and with the gasket pressing tool including a pressing portion biasing body that is disposed between the operation pressing portion of the movement restriction member and the biasing body pressing tubular member and biases the operation pressing portion outward.

(7) The gasket pressing tool according to (6) described above, wherein the gasket pressing tool is configured in such a manner that when the operation pressing portion of the operation unit is pressed, the engagement protrusion moves in an outward direction together with the frame, to release the engagement between the engagement protrusion and the pressing member-side engagement portions of the movement restriction member, and that when the pressing of the operation pressing portion is released, the pressing portion biasing body pushes back the operation pressing portion to cause the engagement protrusion to move in an inward direction together with the frame, to make the engagement protrusion and the pressing member-side engagement portions engage with each other again.

(8) The gasket pressing tool according to (6) or (7) described above, wherein the opening portion of the biasing body pressing tubular member, the operation unit, and the pressing portion biasing body include two opening portions facing each other, two operation units facing each other, and two pressing portion biasing bodies facing each other, respectively.

(9) The gasket pressing tool according to any one of (6) to (8) described above, wherein the biasing body pressing tubular member includes an accommodation portion that accommodates one end portion of the pressing portion biasing body.

(10) The gasket pressing tool according to any one of (1) to (9) described above, wherein the gasket pressing member includes a gap through which the engagement protrusion is able to enter from an outer surface side, the gap being provided between adjacent ones of the pressing member-side engagement portions in the axial direction.

(11) The gasket pressing tool according (1) described above, wherein the gasket pressing member has the engaged state maintaining function with the movement restriction member including a tubular portion that partially encloses the biasing body pressing tubular member and has an inner surface provided with the engagement protrusion, and with the gasket pressing tool including an annular biasing body that is disposed between the biasing body pressing tubular member and the movement restriction member, has one end portion fixed to the biasing body pressing tubular member, has another end portion fixed to the movement restriction member, and maintains the state of engagement between the engagement protrusion and the pressing member-side engagement portions of the gasket pressing member.

(12) The gasket pressing tool according to (11) described above, wherein the gasket pressing tool is configured in such a manner that when the movement restriction member is rotated by a predetermined angle relative to the biasing body pressing tubular member, the engagement between the engagement protrusion and the pressing member-side engagement portions is released, and that when an operation of rotating the movement restriction member is released, the engagement protrusion and the pressing member-side engagement portions are engaged with each other again with the annular biasing body causing reverse rotation of the movement restriction member.

(13) The gasket pressing tool according to (11) or (12) described above, wherein the movement restriction member includes a gap through which the engagement protrusion is able to enter in a circumferential direction, the gap being provided between adjacent ones of the pressing member-side engagement portions.

(14) The gasket pressing tool according to any one of (11) to (13) described above, wherein the engagement protrusion is detached in the circumferential direction from the gap between the adjacent ones of the pressing member-side engagement portions with a rotational operation of the movement restriction member.

(15) The gasket pressing tool according (1) described above, wherein the gasket pressing member has the engaged state maintaining function with the movement restriction member including a tubular portion that partially encloses the biasing body pressing tubular member and has an inner surface provided with the engagement protrusion, and with the gasket pressing tool including an annular biasing body that is disposed between the biasing body pressing tubular member and the movement restriction member, has one end portion fixed to the biasing body pressing tubular member, has another end portion fixed to the movement restriction member, and maintains the state of engagement between the engagement protrusion and the pressing member-side engagement portions of the gasket pressing member, and the gasket pressing tool further includes a tubular operation member attached to a rear end portion of the biasing body pressing tubular member to be movable in the axial direction, and the operation member includes rotation protrusion portion that comes into contact with the movement restriction member and rotates the movement restriction member in a pushing operation toward the distal end side, and an operation member biasing body that is accommodated in the operation member, has a distal end coming into contact with a rear end surface of the biasing body pressing tubular member, and biases the operation member rearward.

(16) The gasket pressing tool according to (15) described above, wherein the gasket pressing tool is configured in such a manner that, when the movement restriction member rotates with the operation member pushed, the engagement between the engagement protrusion of the movement restriction member and the pressing member-side engagement portions is released, and that when the movement restriction member is reversely rotated by the annular biasing body in response to releasing of the pushing of the operation member, the engagement protrusion of the movement restriction member and the pressing member-side engagement portions are engaged with each other again.

(17) The gasket pressing tool according to (15) or (16) described above, wherein the movement restriction member includes an enclosed member-side inclined portion that is provided on an outer surface of the movement restriction member and is formed to be inclined in a rotation direction in which the engagement between the engagement protrusion and the pressing member-side engagement portions is released, and the rotation protrusion portion includes an operation member side inclined portion that, in the pushing operation, comes into sliding contact with the enclosed member-side inclined portion and rotates the movement restriction member.

(18) The gasket pressing tool according to (17) described above, wherein the enclosed member-side inclined portion and the operation member side inclined portion include two enclosed member-side inclined portions facing each other and two operation member side inclined portions facing each other, respectively.

(19) The gasket pressing tool according to any one of (15) to (18) described above, wherein the engagement protrusion is detached in a circumferential direction from the gap between the adjacent ones of the pressing member-side engagement portions, when the operation member is pushed and the movement restriction member is rotated.

(20) The gasket pressing tool according to any one of (15) to (19) described above, wherein the gasket pressing member includes a gap through which the engagement protrusion is able to enter in the circumferential direction, the gap being provided between adjacent ones of the pressing member-side engagement portions.

(21) The gasket pressing tool according to any one of (1) to (20) described above, wherein the biasing body pressing tubular member includes a bar shaped portion that protrudes in the distal end direction from a rear end inner surface and enters into the pressing member biasing body.

Furthermore, the medicine administration tool is as follows.

(22) A medicine administration tool including: a syringe including an outer tube having a rear end portion provided with a flange and a gasket slidably accommodated in the outer tube; and the gasket pressing tool according to any one of (1) to (21) described above.

(23) The medicine administration tool according to (22) described above, wherein the syringe is a prefilled syringe including medicine filling the outer tube and a distal end sealing member of the outer tube, and the medicine administration tool is in a state where the gasket pressing tool is attached to the prefilled syringe.

The detailed description above describes embodiments of a medicine administration tool and a gasket pressing tool representing examples of the medicine administration tool and gasket pressing tool disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A gasket pressing tool configured to move a gasket in a distal end direction of an outer tube of a syringe, the outer tube having a rear end portion provided with a flange, the gasket being slidably accommodated in the outer tube, the gasket pressing tool comprising:
a gasket pressing member configured to press the gasket in the distal end direction;
a syringe attachment member attached to the flange of the outer tube;
a pressing member biasing body having a distal end portion accommodated in the gasket pressing member and having a rear end portion protruding from the gasket pressing member;
a biasing body pressing tubular member that accommodates the rear end portion of the pressing member biasing body and has a flange portion that is provided at a distal end portion of the biasing body pressing tubular member and is accommodated in the syringe attachment member, and an opening portion that is provided proximal to the flange portion; and
a movement restriction member that is held by the biasing body pressing tubular member and/or the syringe attachment member, includes an engagement protrusion that enters into the biasing body pressing tubular member through the opening portion, and restricts a movement of the gasket pressing member, wherein
the gasket pressing member includes a plurality of pressing member-side engagement portions arranged in an axial direction, the pressing member-side engagement portions being capable of engaging with the engagement protrusion of the movement restriction member,
the gasket pressing tool further has an engaged state maintaining function of maintaining a state of engagement between the engagement protrusion of the movement restriction member and the pressing member-side engagement portions of the gasket pressing member, and an engagement protrusion operation function of moving the engagement protrusion to release the engagement between the engagement protrusion and the pressing member-side engagement portion,
the gasket pressing tool has the engaged state maintaining function with the movement restriction member including an operation unit that includes a distal end portion held by the biasing body pressing tubular member and/or the syringe attachment member, the engagement protrusion that is provided more on a rear side than the distal end portion of the operation unit and is provided in one end portion, an operation pressing portion, and a frame coupling the engagement protrusion and the operation pressing portion to each other, and with the gasket pressing tool including a pressing portion biasing body that is disposed between the operation pressing portion of the movement restriction member and the biasing body pressing tubular member and biases the operation pressing portion outward, and
the operation unit is configured such that movement of the operation pressing portion toward the pressing-member side engagement portion by moving inward in a first direction causes movement of the engagement protrusion away from the pressing-member side engagement portion by moving outward in the first direction.

2. The gasket pressing tool according to claim 1, wherein the opening portion of the biasing body pressing tubular member and the engagement protrusion of the movement restriction member include two opening portions facing each other and two engagement protrusions facing each other, respectively.

3. The gasket pressing tool according to claim 1, wherein the gasket pressing tool is configured in such a manner that when the operation pressing portion of the operation unit is pressed, the engagement protrusion moves in an outward direction together with the frame, to release the engagement between the engagement protrusion and the pressing member-side engagement portions of the movement restriction member, and that when the pressing of the operation pressing portion is released, the pressing portion biasing body pushes back the operation pressing portion to cause the engagement protrusion to move in an inward direction together with the frame, to make the engagement protrusion and the pressing member-side engagement portions engage with each other again.

4. The gasket pressing tool according to claim 1, wherein the opening portion of the biasing body pressing tubular member, the operation unit, and the pressing portion biasing body include two opening portions facing each other, two operation units facing each other, and two pressing portion biasing bodies facing each other, respectively.

5. The gasket pressing tool according to claim 1, wherein the biasing body pressing tubular member includes an accommodation portion that accommodates one end portion of the pressing portion biasing body.

6. The gasket pressing tool according to claim 1, wherein the gasket pressing member includes a gap through which the engagement protrusion is able to enter from an outer surface side, the gap being provided between adjacent ones of the pressing member-side engagement portions in the axial direction.

* * * * *